US011299470B2

(12) United States Patent
Colton et al.

(10) Patent No.: US 11,299,470 B2
(45) Date of Patent: Apr. 12, 2022

(54) SYSTEMS AND METHODS FOR SEPARATING CANNABIS-DERIVED COMPOUNDS USING CHROMATOGRAPHY WITH LIQUID OR SUPERCRITICAL CARBON DIOXIDE

(71) Applicant: Massachusetts Institute of Technology, Cambridge, MA (US)

(72) Inventors: Clark K. Colton, Newton, MA (US); John M. Moses, Milton, MA (US); Veronica M. Wilson, Ann Arbor, MI (US); William H. Dalzell, Marshfield, MA (US); Mariya Layurova, Cambridge, MA (US); Tony J. Elian, San Mateo, CA (US); Truong H. Cai, Providence, RI (US); John MacKay, Whitinsville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/637,256

(22) PCT Filed: Aug. 7, 2018

(86) PCT No.: PCT/US2018/045656
§ 371 (c)(1),
(2) Date: Feb. 6, 2020

(87) PCT Pub. No.: WO2019/032609
PCT Pub. Date: Feb. 14, 2019

(65) Prior Publication Data
US 2020/0247773 A1 Aug. 6, 2020

Related U.S. Application Data

(60) Provisional application No. 62/542,248, filed on Aug. 7, 2017, provisional application No. 62/542,239, filed on Aug. 7, 2017.

(51) Int. Cl.
*C07D 311/80* (2006.01)
*C07D 311/78* (2006.01)
*C07C 37/00* (2006.01)

(52) U.S. Cl.
CPC .......... *C07D 311/80* (2013.01); *C07C 37/004* (2013.01); *C07D 311/78* (2013.01)

(58) Field of Classification Search
CPC .... C07D 311/80; C07D 311/78; C07C 37/004
See application file for complete search history.

(56) References Cited

U.S. PATENT DOCUMENTS 6,403,126 B1 * 6/2002 Webster ............... A61K 36/185
424/725
10,568,863 B2    2/2020  Rutz 2004/0049059 A1    3/2004  Mueller
2007/0276031 A1 * 11/2007 Geiser .................. C07D 311/80
514/454
2008/0103193 A1 *  5/2008  Castor .................. C07D 311/80
514/454
2014/0248379 A1    9/2014  Mueller
2017/0189831 A1    7/2017  James et al.

FOREIGN PATENT DOCUMENTS

EP        3061510 A1     8/2016
WO    WO 2005/061480 A1  7/2005
WO    WO 2016/187679 A1  12/2016

OTHER PUBLICATIONS

International Search Report and Written Opinion for PCT/US2018/045656 dated Nov. 21, 2018.
International Preliminary Report on Patentability for PCT/US2018/045656 dated Feb. 20, 2020.
[No. Author Listed] ICH guideline Q3C (R6) on Impurities: Guideline for Residual Solvents, Step 5, Aug. 9, 2019, EMA/CHMP/ICH/82260/2006 European Medicines Agency.
[No. Author Listed] Legal Cannabis—Supercritical Fluid Chromatography Could Be the Answer. Chromatography Today. Sep. 9, 2015. Retrieved from https://www.chromatographytoday.com/news/supercritical-fluid-sfegreen-chromatography/45/breaking-news/legal-cannabis-mdash-supercritical-fluid-c%E2%80%A6.

(Continued)

*Primary Examiner* — Timothy R Rozof
(74) *Attorney, Agent, or Firm* — Wolf, Greenfield & Sacks, P.C.

(57) ABSTRACT

Chromatography systems and methods for using carbon dioxide to separate one or more cannabis-derived compounds from other components of a mixture are generally described. Some of the methods described herein comprise transporting a mixture comprising a first cannabis-derived compound and one or more other components through a chromatography column containing a stationary phase comprising a packing material. In some embodiments, the mixture is transported through the column within a mobile phase that comprises carbon dioxide (e.g., supercritical $CO_2$, liquid $CO_2$). The mobile phase may be substantially free of a co-solvent that is in liquid phase at standard room temperature and pressure. In some embodiments, the mobile phase is free of any co-solvent and comprises 100 vol % carbon dioxide. The first cannabis-derived compound may interact with the stationary phase and/or the mobile phase to a different degree than the one or more other components of the mixture, causing at least partial separation of the first cannabis-derived compound from the one or more other components within the column. Due to this separation, at least one fraction of the mobile phase that comprises the first cannabis-derived compound and is substantially free of the one or more other components of the mixture may be collected.

23 Claims, 14 Drawing Sheets

(56) References Cited

OTHER PUBLICATIONS

[No. Author Listed], 467. Organic Volatile Impurities., Residual Solvent Limits, U.S. Pharmacopeia, USP29-NF24.

Ashraf-Khorassani et al., Supercritical fluid extraction of Kava lactones from Kava root and their separation via supercritical fluid chromatography. Chromatographia. 1999;50, pp. 287-292(1999).

Backstrom et al., A preliminary study of the analysis of Cannabis by supercritical fluid chromatography with atmospheric pressure chemical ionization mass spectroscopic detection. Science & Justice 37(2): 91-97, 1997.

Bamba, Application of supercritical fluid chromatography to the analysis of hydrophobic metabolites. J. Sep. Sci 31: 1274-1278, 2008.

Breitenbach et al., Assessment of ultra high performance supercritical fluid chromatography as a separation technique for the analysis of seized drugs: Applicability to synthetic cannabinoids. J. Chromatography A 1440: 201-211, 2016.

Buskov et al., Supercritical fluid chromatography as a method of analysis for the determination of 4-hydroxybenzylglucosinolate degradation products. J. Biochem. Biophys. Methods 43: 157-174, 2000.

Chou et al., Using subcritical/supercritical fluid chromatography to separate acidic, basic, and neutral compounds over an ionic liquid-functionalized stationary phase. J. Chromatography A 1216: 3594-3599, 2009.

Cole, Analysis of Cannabis by supercritical fluid chromatography with ultraviolet detection. Methods in Biotechnology 13: 145-148, 2000.

Dolak, Carbon dioxide chromatography: The role of SFC in pharmaceutical discovery. Today's Chemist at Work, pp. 47-48, Oct. 2004.

Foley et al., Supercritical Fluid Chromatography for the Analysis of Natural Products. Chapter 4. Modern Phytochemical Methods. Ed(s) Fischer et al. Plenum Press. 1991. 113-147.

Fornstedt, Peak distortions in preparative supercritical fluid chromatography—a more complete overview. Chromatography Today, Sep. 6, 2016.

Geryk et al., A supercritical fluid chromatography method for the systematic toxicology analysis of cannabinoids and their metabolites. Anal. Methods. 7: 6056-6059, 2015.

Gopaliya et al., A review article on supercritical fluid chromatography. Intl. J. of Pharma Research & Review 3(5): 59-66, 2014.

Hartmann et al., Supercritical Fluid Chromatography—Theoretical Background and Applications on Natural Products. Planta Med. Nov. 2015;81(17):1570-81. doi: 10.1055/s-0035-1545911. Epub Apr. 23, 2015. PMID: 25905595.

Ibañez et al., Tuning of mobile and stationary phase polarity for the separation of polar compounds by SFC. J. Biochem. Biophys. Methods 43: 25-43, 2000.

Kalíkova et al., Supercritical fluid chromatography as a tool for enantioselective separation; a review. Anal Chim Acta. Apr. 22, 2014;821:1-33. doi: 10.1016/j.aca.2014.02.036. Epub Feb. 28, 2014. PMID: 24703210.

Klesper et al., High pressure gas chromatography above critical temperatures. J. Org. Chem. 27: 700-701, 1962.

McDonald, A Sample Preparation Primer and Guide to Solid Phase Extraction Methods Development. 2001. Eds(McDonald et al.) www.waters.com.

Mclaren et al., Dense-gas chromatography of nonvolatile substances of high molecular weight. Science. Jan. 12, 1968;159(3811):197-9. doi: 10.1126/science.159.3811.197. PMID: 5634909.

Nováková et al., Modern analytical supercritical fluid chromatography using columns packed with sub-2 µm particles: A tutorial. Analytical Chimica Acta. 824: 18-35, 2014.

Ren-Qi et al., Recent advances in pharmaceutical separations with supercritical fluid chromatography using chiral stationary phases. Trends Analyt Chem. 2012;37:83-100.

Runco et al., The separation of $\Delta^8$-THC, $\Delta^9$-THC, and their enantiomers by UPC$^2$ using trefoil chiral columns. Waters Corporation, Milford, MA, Sep. 2016. www.waters.com/webassets/cms/library/docs/720005812en.pdf.

Runco et al., Simple method development for the separation of chiral synthetic cannabinoids using ultra high performance critical fluid chromatography. Chromatography Today, Sep. 6, 2016.

Shaimi et al., Injection by Extraction: A Novel Sample Introduction Technique for Preparative SFC. Chromatography Today. 2014. 42-45.

Toyo'oka et al., A reliable method for the separation and detection of synthetic cannabinoids by supercritical fluid chromatography with mass spectrometry, and its application to plant products. Chem. Pharm. Bull. 63: 762-769, 2015.

Wang et al., Quantitative determination of cannabinoids in cannabis and cannabis products using ultra-high-performance supercritical fluid chromatography and diode array/mass spectrometric detection. J. Forensic Sci 62(3): 602-611, 2017.

Wells et al., Unified chromatography with $CO_2$-based binary mobile phases: Exploring chromatographic schemes involving binary mobile phases with $CO_2$. Analytical Chem. 75: 18A-24A, 2003.

* cited by examiner

SYSTEMS AND METHODS FOR SEPARATING CANNABIS-DERIVED COMPOUNDS USING CHROMATOGRAPHY WITH LIQUID OR SUPERCRITICAL CARBON DIOXIDE

RELATED APPLICATIONS

This application is a national stage filing under 35 U.S.C. § 371 of International Patent Application Serial No. PCT/US2018/045656, filed Aug. 7, 2018, and entitled "Systems and Methods for Separating Cannabis-Derived Compounds Using Chromatography with Liquid or Supercritical Carbon Dioxide," which claims priority under 35 U.S.C. § 119(e) to U.S. Provisional Patent Application Ser. No. 62/542,239, filed Aug. 7, 2017, and entitled "Systems and Methods for Separating Cannabis-Derived Compounds Using Chromatography with Liquid or Supercritical Carbon Dioxide," and U.S. Provisional Patent Application Ser. No. 62/542,248, filed Aug. 7, 2017, and entitled "Systems and Methods for Separating Cannabis-Derived Compounds Using Chromatography with Substantially Pure Carbon Dioxide," each of which is incorporated herein by reference in its entirety for all purposes.

FIELD

The present invention generally relates to systems and methods of separating and purifying cannabis-derived compounds using chromatography with liquid or supercritical carbon dioxide.

BACKGROUND

Cannabis-derived compounds have increasingly been recognized as having a number of medicinal benefits, including reducing pain and/or nausea, treating epilepsy, and slowing the rate of tumor growth. To meet growing demand for pure individual cannabis-derived compounds, there is a need for systems and methods for separating certain cannabis-derived compounds from mixtures comprising one or more other components.

Chromatography methods employing a mobile phase comprising supercritical carbon dioxide have previously been used to separate cannabinoids, but the prior art studies employed polar liquid co-solvents (e.g., methanol, ethanol) to enhance the solubility of the cannabinoids in the mobile phase. Since the polar liquid co-solvents are typically flammable and/or toxic and, therefore, are not suitable for human consumption or use, the products of these prior art chromatography methods typically require further purification to remove the co-solvent, typically by heating and potentially denaturing the desired component. Accordingly, improved chromatography methods for separating cannabis-derived compounds, which do not use toxic solvents or denature naturally occurring components, are desirable.

SUMMARY

The present invention generally relates to systems and methods of separating and purifying cannabis-derived compounds using chromatography with liquid or supercritical carbon dioxide. The subject matter of the present invention involves, in some cases, interrelated products, alternative solutions to a particular problem, and/or a plurality of different uses of one or more systems and/or articles.

Some aspects are directed to a chromatography method for purifying a cannabis-derived compound from a mixture. In some embodiments, the method comprises transporting the mixture, which comprises a first component and a second component, through a chromatography column containing a stationary phase comprising a packing material. In certain embodiments, the first component comprises a first cannabis-derived compound. In certain embodiments, the mixture is transported within a mobile phase that comprises carbon dioxide and is substantially free of a co-solvent that is in liquid phase at standard room temperature and pressure. In certain embodiments, the mixture is transported through the column and in contact with the stationary phase. In certain embodiments, the first component and the second component of the mixture are each transported within the mobile phase substantially continuously from a first end of the column to a second end of the column. In some embodiments, the method comprises collecting from the second end of the column a first fraction of the mobile phase comprising the first component over a first time interval, wherein the first fraction is substantially free of the second component. In some embodiments, the method comprises collecting from the second end of the column a second fraction of the mobile phase comprising the second component over a second time interval different from the first time interval, wherein the second fraction is substantially free of the first component.

Some aspects are directed to purifying a first cannabis-derived compound from a mixture. In some embodiments, the system comprises a chromatography column containing a stationary phase comprising a packing material. In some embodiments, the system comprises a mobile phase comprising carbon dioxide. In certain embodiments, the mobile phase is substantially free of a co-solvent that is in liquid phase at standard room temperature and pressure. In some embodiments, the system comprises the mixture, wherein the mixture comprises a first component and a second component. In certain embodiments, the first component comprises the first cannabis-derived compound.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
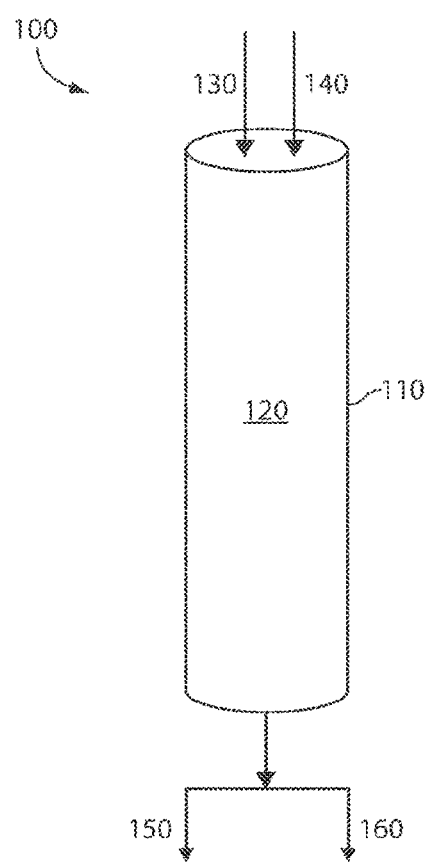
FIG. 1 shows, according to some embodiments, a schematic diagram of an exemplary chromatography system comprising a chromatography column, a stationary phase, a mobile phase, and a mixture comprising a cannabis-derived compound.

Chromatography systems and methods for using carbon dioxide to separate one or more cannabis-derived compounds from other components of a mixture are generally described. Some of the methods described herein comprise transporting a mixture comprising a first cannabis-derived compound and one or more other components through a chromatography column containing a stationary phase comprising a packing material. In some embodiments, the mixture is transported through the column within a mobile phase that comprises liquid or supercritical carbon dioxide. The mobile phase may be substantially free of a co-solvent that is in liquid phase at standard room temperature and pressure ("standard room temperature and pressure" as used herein refers to a temperature of 20° C. and a pressure of 14.7 psia). In some embodiments, the mobile phase is free of any co-solvent and comprises 100 vol % carbon dioxide. The first cannabis-derived compound may interact with the stationary phase and/or the mobile phase to a different degree than the one or more other components of the mixture, causing at least partial separation of the first cannabis-derived compound from the one or more other components within the column. Due to this separation, at least one fraction of the mobile phase that comprises the first cannabis-derived compound and is substantially free of the one or more other components of the mixture may be collected.

In some cases, it may be desirable to obtain substantially pure cannabis-derived compounds since certain cannabis-derived compounds have been associated with therapeutic and/or psychoactive effects in humans. For example, certain cannabis-derived compounds have been used to treat conditions including, but not limited to, glaucoma, epilepsy (e.g., child epilepsy and seizures, adult epilepsy and seizures), severe or chronic pain, migraines, cancer, HIV, cachexia (i.e., wasting syndrome), multiple sclerosis, PTSD, hepatitis C, ALS, Crohn's disease, Alzheimer's disease, arthritis, fibromyalgia, inflammation, and stress. These compounds continue to be studied for numerous other health and medicinal applications.

However, conventional methods of purifying cannabis-derived compounds have generally been associated with certain drawbacks. For example, one known chromatography method involves using supercritical carbon dioxide with a liquid co-solvent (i.e., a co-solvent that is in liquid phase at standard room temperature and pressure) as a mobile phase. Due to the apolarity of carbon dioxide, polar compounds such as cannabis-derived compounds often are only slightly soluble in carbon dioxide, which it was conventionally believed rendered supercritical carbon dioxide ($sCO_2$) unsuitable for use as a chromatographic mobile phase to separate mixtures comprising those compounds. In certain known chromatography methods, a liquid co-solvent, which may be a polar liquid co-solvent, has been added to $sCO_2$ to enhance the solubility of polar compounds in a $sCO_2$-containing mobile phase. However, when a polar liquid co-solvent (e.g., methanol, ethanol, acetonitrile) is added to a $sCO_2$-containing mobile phase, additional purification steps are generally required to remove the polar liquid co-solvent from any collected fractions since the polar liquid co-solvents are often toxic and/or flammable.

The inventors have surprisingly found that one or more cannabis-derived compounds can be separated from other components of a mixture through a chromatography method that uses a mobile phase that comprises carbon dioxide (e.g., supercritical $CO_2$, liquid $CO_2$) and is substantially free of a co-solvent that is in liquid phase at standard room temperature and pressure. The inventors have further recognized and appreciated that one or more cannabis-derived compounds can be separated though a chromatography method that uses a mobile phase that comprises carbon dioxide and is substantially free of any co-solvent. In some cases, the chromatography methods are performed under conditions that result in the carbon dioxide of the mobile phase having a relatively high density. This relatively high density of the carbon dioxide may advantageously increase the solubility of polar compounds, such as certain cannabis-derived compounds, within the mobile phase. Such methods may advantageously require fewer steps than conventional chromatography methods (e.g., methods using a mobile phase that comprises carbon dioxide and a liquid co-solvent) as the carbon dioxide can simply evaporate from any collected fractions (e.g., fractions comprising the one or more cannabis-derived compounds) at standard room temperature and pressure. Accordingly, additional purification steps may not be required.

Certain embodiments described herein relate to chromatography systems and methods for separating a cannabis-derived compound from a mixture. Chromatography generally refers to a separation process involving two phases, one stationary and one mobile. A schematic diagram of exemplary chromatography system 100 is illustrated in FIG. 1. As shown in FIG. 1, system 100 comprises column 110 containing stationary phase 120, which comprises a packing material. As described in further detail below, the packing material may comprise a porous solid. System 100 may further comprise mobile phase 130, which may comprise carbon dioxide (e.g., supercritical $CO_2$, liquid $CO_2$) and be substantially free of a co-solvent that is in liquid phase at standard room temperature and pressure. In addition, system 100 may comprise mixture 140 comprising a first component and a second component, where the first component comprises a first cannabis-derived compound. System 100 may be configured to separate the first component from at least the second component of the mixture.

In operation, mobile phase 130 may flow from a first end of column 110 to a second end of column 110. Mixture 140 may be injected into the first end of column 110 and may be transported through column 110 within mobile phase 130 and in contact with stationary phase 120. As mixture 140 is transported from the first end of column 110 to the second end of column 110, the first component and the second component of mixture 140 may interact with stationary phase 120 and mobile phase 130 to different degrees such that the first component is at least partially separated from the second component within the column. For example, if the first component interacts more strongly than the second component with stationary phase 120, the first component may take a longer amount of time to travel from the first end to the second end of column 110. Conversely, if the second component interacts more strongly than the first component with stationary phase 120, the second component may take a longer amount of time to travel from the first end to the second end of column 110. The first component and the second component may each be transported within mobile phase 130 substantially continuously from the first end to the second end of column 110.

In some embodiments, a first fraction 150 comprising the first component and substantially free of the second component is collected from the second end of column 110 over a first time interval. In some embodiments, a second fraction 160 comprising the second component and substantially free of the first component is collected from the second end of column 110 over a second, non-overlapping time interval that is different from the first time interval. First fraction 150 may be collected before or after second fraction 160. In some embodiments, mobile phase 130 may flow substantially continuously through column 110 until at least first fraction 150 and second fraction 160 are collected. In some instances, first fraction 150 and/or second fraction 160 are analyzed using an analytical instrument (e.g., an ultraviolet-visible (UV-Vis) spectrophotometer), and a chromatogram comprising one or more peaks may be obtained.

As described above, the chromatography system may comprise a mixture. The mixture may comprise any number of components (e.g., distinct chemical compounds). In some embodiments, the mixture comprises at least a first component and a second component, and the chromatography system may be configured to separate the first component from at least the second component. In addition to the first component and the second component, the mixture may comprise any number of additional components. In certain embodiments, for example, the mixture comprises at least about 2 components, at least about 3 components, at least about 4 components, at least about 5 components, at least about 10 components, at least about 20 components, at least about 50 components, at least about 100 components, at least about 150 components, at least about 200 components, or at least about 500 components. In some embodiments, the mixture comprises between about 2 and about 500 components, between about 5 and about 500 components, between about 10 and about 500 components, between about 20 and about 500 components, between about 50 and about 500 components, between about 100 and about 500 components, or between about 200 and about 500 components.

In some embodiments, the first component comprises a first cannabis-derived compound. A cannabis-derived compound generally refers to a compound that can be found in a *Cannabis* species plant (e.g., *Cannabis sativa, Cannabis indica, Cannabis ruderalis*). Examples of cannabis-derived compounds include, but are not limited to, cannabinoids, terpenes and terpenoids, trichomes, resins, and waxes. Cannabinoids generally refer to chemical compounds that interact with an endocannabinoid system (e.g., a CB1 endocannabinoid system, a CB2 endocannabinoid system). In some cases, for example, a cannabinoid may bind to one or more cannabinoid receptors in a cell.

Figure 2A:
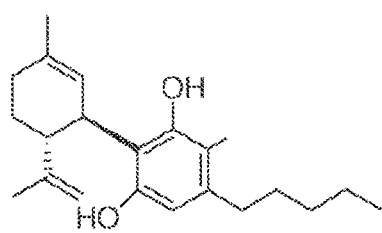
FIG. 2A shows an exemplary representation of the chemical structure of cannabidiol (CBD), according to some embodiments.
Figure 2B:
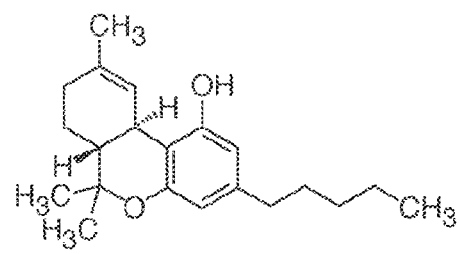
FIG. 2B shows an exemplary representation of the chemical structure of tetrahydrocannabinol (THC), according to some embodiments.
Figure 2C:
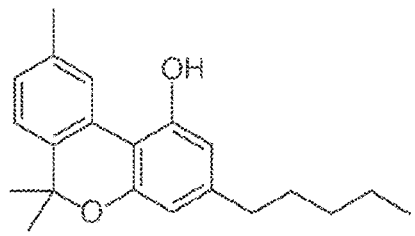
FIG. 2C shows an exemplary representation of the chemical structure of cannabinol (CBN), according to some embodiments.
Figure 2D:
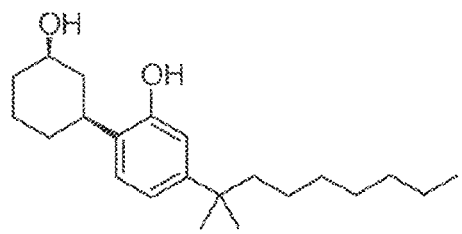
FIG. 2D shows an exemplary representation of the chemical structure of CP-47497, according to some embodiments.

The first cannabis-derived compound may be any suitable type of cannabis-derived compound. In some instances, the first cannabis-derived compound comprises a first cannabinoid. The first cannabinoid may be any suitable type of cannabinoid. Examples of suitable types of cannabinoids include, but are not limited to, tetrahydrocannabinol-type cannabinoids, iso-tetrahydrocannabinol-type cannabinoids, cannabidiol-type cannabinoids, cannabigerol-type cannabinoids, cannabichromene-type cannabinoids, cannabielsoin-type cannabinoids, cannabicyclol-type cannabinoids, and cannabicitran-type cannabinoids. The first cannabinoid may be any suitable cannabinoid. Non-limiting examples of suitable cannabinoids include cannabidiol (CBD), cannabinol (CBN), tetrahydrocannabinol (THC), CP-47497, cannabigerol, tetrahydrocannabivarin, cannabidivarin, and cannabichromene. The chemical structures of certain exemplary cannabinoids are shown in FIG. 2. In particular, FIG. 2A shows the chemical structure of CBD, FIG. 2B shows the chemical structure of THC, FIG. 2C shows the chemical structure of CBN, and FIG. 2D shows the chemical structure of CP-47497.

The mixture, prior to injection into a chromatography column, may have any concentration of the first cannabis-derived compound. In some embodiments, the concentration of the first cannabis-derived compound in the mixture is at least about 0.5 ng/mL, at least about 1 ng/mL, at least about 10 ng/mL, at least about 100 ng/mL, at least about 500 ng/mL, at least about 500 ng/mL, at least about 1,000 ng/mL, at least about 5,000 ng/mL, at least about 10,000 ng/mL, at least about 50,000 ng/mL, at least about 0.1 mg/mL, at least about 0.5 mg/mL, at least about 1 mg/mL, at least about 2 mg/mL, at least about 5 mg/mL, at least about 10 mg/mL, at least about 20 mg/mL, at least about 50 mg/mL, at least about 100 mg/mL, at least about 500 mg/mL, or at least about 1,000 mg/mL. In some embodiments, the concentration of the first cannabis-derived compound in the mixture is in a range between about 0.5 ng/mL and about 10 ng/mL, between about 0.5 ng/mL and about 100 ng/mL, between about 0.5 ng/mL and about 1,000 ng/mL, between about 0.5 ng/mL and about 10,000 ng/mL, between about 0.5 ng/mL and about 0.1 mg/mL, between about 0.5 ng/mL and about 1 mg/mL, between about 0.5 ng/mL and about 10 mg/mL, between about 0.5 ng/mL and about 100 mg/mL, between about 0.5 ng/mL and about 1,000 mg/mL, between about 0.1 mg/mL and about 1 mg/mL, between about 0.1 mg/mL and about 10 mg/mL, between about 0.1 mg/mL and about 100 mg/mL, between about 0.1 mg/mL and about 1,000 mg/mL, between about 1 mg/mL and about 10 mg/mL, between about 1 mg/mL and about 100 mg/mL, between about 1 mg/mL and about 1,000 mg/mL, between about 5 mg/mL and about 10 mg/mL, between about 5 mg/mL and about 100 mg/mL, between about 5 mg/mL and about 1,000 mg/mL, between about 10 mg/mL and about 100 mg/mL, between about 10 mg/mL and about 1,000 mg/mL, between about 20 mg/mL and about 100 mg/mL, between about 20 mg/mL and about 1,000 mg/mL, between about 50 mg/mL and about 100 mg/mL, between about 50 mg/mL and about 1,000 mg/mL, or between about 100 mg/mL and about 1,000 mg/mL. The concentration of a component (e.g., the first cannabis-derived compound) of the mixture may be measured according to any method known in the art. An exemplary method of measuring concentration of a component in the mixture is high-performance liquid chromatography (HPLC).

In some embodiments, the second component comprises a second cannabis-derived compound. The second cannabis-derived compound may be any suitable type of cannabinoid. Examples of suitable types of cannabinoids include, but are not limited to, tetrahydrocannabinol-type cannabinoids, iso-tetrahydrocannabinol-type cannabinoids, cannabidiol-type cannabinoids, cannabigerol-type cannabinoids, cannabichromene-type cannabinoids, cannabielsoin-type cannabinoids, cannabicyclol-type cannabinoids, and cannabicitran-type cannabinoids. The second cannabinoid may be any suitable cannabinoid. Non-limiting examples of suitable cannabinoids include cannabidiol (CBD), cannabinol (CBN), tetrahydrocannabinol (THC), cannabigerol, tetrahydrocannabivarin, cannabidivarin, and cannabichromene.

The mixture, prior to injection into a chromatography column, may have any concentration of the second cannabis-derived compound. In some embodiments, the concentration of the second cannabis-derived compound in the mixture is at least about 0.5 ng/mL, at least about 1 ng/mL, at least about 10 ng/mL, at least about 100 ng/mL, at least about 500 ng/mL, at least about 500 ng/mL, at least about 1,000 ng/mL, at least about 5,000 ng/mL, at least about 10,000 ng/mL, at least about 50,000 ng/mL, at least about 0.1 mg/mL, at least about 0.5 mg/mL, at least about 1 mg/mL, at least about 2 mg/mL, at least about 5 mg/mL, at least about 10 mg/mL, at least about 20 mg/mL, at least about 50 mg/mL, at least about 100 mg/mL, at least about 500 mg/mL, or at least about 1,000 mg/mL. In some embodiments, the concentration of the second cannabis-derived compound in the mixture is in a range between about 0.5 ng/mL and about 10 ng/mL, between about 0.5 ng/mL and about 100 ng/mL, between about 0.5 ng/mL and about 1,000 ng/mL, between about 0.5 ng/mL and about 10,000 ng/mL, between about 0.5 ng/mL and about 0.1 mg/mL, between about 0.5 ng/mL and about 1 mg/mL, between about 0.5 ng/mL and about 10 mg/mL, between about 0.5 ng/mL and about 100 mg/mL, between about 0.5 ng/mL and about 1,000 mg/mL, between about 0.1 mg/mL and about 1 mg/mL, between about 0.1 mg/mL and about 10 mg/mL, between about 0.1 mg/mL and about 100 mg/mL, between about 0.1 mg/mL and about 1,000 mg/mL, between about 1 mg/mL and about 10 mg/mL, between about 1 mg/mL and about 100 mg/mL, between about 1 mg/mL and about 1,000 mg/mL, between about 5 mg/mL and about 10 mg/mL, between about 5 mg/mL and about 100 mg/mL, between about 5 mg/mL and about 1,000 mg/mL, between about 10 mg/mL and about 100 mg/mL, between about 10 mg/mL and about 1,000 mg/mL, between about 20 mg/mL and about 100 mg/mL, between about 20 mg/mL and about 1,000 mg/mL, between about 50 mg/mL and about 100 mg/mL, between about 50 mg/mL and about 1,000 mg/mL, or between about 100 mg/mL and about 1,000 mg/mL.

In some embodiments, the mixture may comprise a third component comprising a third cannabis-derived compound (e.g., a third cannabinoid), a fourth component comprising a fourth cannabis-derived compound (e.g., a fourth cannabinoid), or any number of additional components comprising additional cannabis-derived compounds. Each cannabis-derived compound may be any cannabis-derived compound described herein and may be present in the mixture in any of the concentrations described above with respect to the first and second cannabis-derived compounds.

The mixture may be extracted from a *Cannabis* species plant (e.g., *Cannabis sativa, Cannabis indica, Cannabis ruderalis*) or may be a product of a chemical synthesis. In embodiments in which the mixture is extracted from a *Cannabis* species plant, the mixture may be extracted from one or more components of the *Cannabis* species plant, including any component or subcomponent of a leaf, stalk, flower, stem, root, seed, or any other part of a *Cannabis* species plant. In some cases, a crude extract of a *Cannabis* species plant may be fractionated (e.g., by reducing the extract pressure), and the mixture may comprise a fractionated product. As used herein, the term "*Cannabis* species" refers to both a single species of *Cannabis* and two or more species of *Cannabis* forming a blend.

In some embodiments, the chromatography system comprises a chromatography column. The chromatography column may have any size and shape. In certain cases, for example, the chromatography column comprises a substantially cylindrical tube. The chromatography column may be formed of any suitable material. Non-limiting examples of suitable materials include glass, plastic, a metal or metal alloy (e.g., stainless steel), and a ceramic.

In some embodiments, the chromatography column contains a stationary phase comprising a packing material. Packing material generally refers to material comprising porous solid particles that can be packed into a column. The packing material may be selected based on the components of the mixture to be separated, as different packing materials may have different interactions with mixture components (e.g., a nonpolar component may exhibit greater affinity for a hydrophobic packing material than a hydrophilic packing material). In certain embodiments, the packing material is substantially hydrophilic. Examples of suitable hydrophilic packing materials include, but are not limited to, silica and ethylene-bridged hybrid 2-ethylpyridine (BEH-2-EP). In certain embodiments, the packing material is substantially hydrophobic. A non-limiting example of a suitable hydrophobic packing material is silica coated with $C_{18}$ (referred to simply as $C_{18}$).

The packing material particles may have any suitable size. In some embodiments, the packing material particles have an average particle size of at least about 1 μm, at least about 2 μm, at least about 3 μm, at least about 4 μm, at least about 5 μm, at least about 10 μm, at least about 20 μm, or at least about 50 μm. In some embodiments, the packing material particles have an average particle size of about 50 μm or less, about 20 μm or less, about 10 μm or less, about 5 μm or less, about 4 μm or less, about 3 μm or less, about 2 μm or less, or about 1 μm or less. In some embodiments, the packing material particles have an average particle size in a range between about 1 μm and about 2 μm, between about 1 μm and about 3 μm, between about 1 μm and about 4 μm, between about 1 μm and about 5 μm, between about 1 μm and about 10 μm, between about 1 μm and about 20 μm, or between about 1 μm and about 50 μm. The average particle size of the packing material particles may be determined using laser diffraction particle size measurement techniques or other established techniques.

The packing material particles may have any suitable pore size. In some embodiments, the packing material particles have a pore size of at least about 30 angstroms (Å), at least about 40 Å, at least about 50 Å, at least about 60 Å, at least about 70 Å, at least about 80 Å, at least about 90 Å, at least about 100 Å, at least about 200 Å, at least about 500 Å, or at least about 1,000 Å. In certain embodiments, the packing material particles have a pore size of about 1,000 Å or less, about 500 Å or less, about 200 Å or less, about 100 Å or less, about 90 Å or less, about 80 Å or less, about 70 Å or less, about 60 Å or less, about 50 Å or less, about 40 Å or less, or about 30 Å or less. According to some embodiments, the packing material particles have a pore size in a range between about 30 Å and about 40 Å, between about 30 Å and about 50 Å, between about 30 Å and 100 Å, between about 30 Å and about 200 Å, between about 30 Å and about 500 Å, between about 30 Å and about 1,000 Å, between about 40 Å and about 50 Å, between about 40 Å and about 100 Å, between about 40 Å and about 200 Å, between about 40 Å and about 500 Å, between about 40 Å and about 1,000 Å, between about 50 Å and about 60 Å, between about 50 Å and about 70 Å, between about 50 Å and about 80 Å, between about 50 Å and about 90 Å, between about 50 Å and about 100 Å, between about 50 Å and about 200 Å, between about 50 Å and about 500 Å, between about 50 Å and about 1,000 Å, between about 100 Å and about 500 Å, between about 100 Å and about 1,000 Å, or between about 500 Å and about 1,000 Å. The pore size of the packing material particles may be determined using gas adsorption analysis techniques and calculations, where the uptake of gas or vapors (e.g., $N_2$ or $CO_2$) by a material is measured.

The packing material particles may have any suitable surface area. According to certain embodiments, the packing material particles have a surface area of at least about 20 $m^2/g$, at least about 50 $m^2/g$, at least about 100 $m^2/g$, at least about 150 $m^2/g$, at least about 200 $m^2/g$, at least about 250 $m^2/g$, at least about 300 $m^2/g$, at least about 350 $m^2/g$, at least about 400 $m^2/g$, at least about 450 $m^2/g$, at least about 500 $m^2/g$, at least about 600 $m^2/g$, or at least about 700 $m^2/g$. In some embodiments, the packing material particles have a surface area of about 700 $m^2/g$ or less, about 600 $m^2/g$ or less, about 500 $m^2/g$ or less, about 450 $m^2/g$ or less, about 400 $m^2/g$ or less, about 350 $m^2/g$ or less, about 300 $m^2/g$ or less, about 250 $m^2/g$ or less, about 200 $m^2/g$ or less, about 150 $m^2/g$ or less, about 100 $m^2/g$ or less, about 50 $m^2/g$ or less, about 20 $m^2/g$ or less. According to some embodiments, the packing material particles have a surface area in a range between about 20 $m^2/g$ and about 50 $m^2/g$, between about 20 $m^2/g$ and about 100 $m^2/g$, between about 20 $m^2/g$ and about 200 $m^2/g$, between about 20 $m^2/g$ and about 300 $m^2/g$, between about 20 $m^2/g$ and about 400 $m^2/g$, between about 20 $m^2/g$ and about 500 $m^2/g$, between about 20 $m^2/g$ and about 600 $m^2/g$, between about 20 $m^2/g$ and about 700 $m^2/g$, between about 50 $m^2/g$ and about 100 $m^2/g$, between about 50 $m^2/g$ and about 200 $m^2/g$, between about 50 $m^2/g$ and about 300 $m^2/g$, between about 50 $m^2/g$ and about 400 $m^2/g$, between about 50 $m^2/g$ and about 500 $m^2/g$, between about 50 $m^2/g$ and about 600 $m^2/g$, between about 50 $m^2/g$ and about 700 $m^2/g$, between about 100 $m^2/g$ and about 150 $m^2/g$, between about 100 $m^2/g$ and about 200 $m^2/g$, between about 100 $m^2/g$ and about 300 $m^2/g$, between about 100 $m^2/g$ and about 400 $m^2/g$, between about 100 $m^2/g$ and about 500 $m^2/g$, between about 100 $m^2/g$ and about 600 $m^2/g$, between about 100 $m^2/g$ and about 700 $m^2/g$, between about 200 $m^2/g$ and about 300 $m^2/g$, between about 200 $m^2/g$ and about 400 $m^2/g$, between about 200 $m^2/g$ and about 500 $m^2/g$, between about 200 $m^2/g$ and about 600 $m^2/g$, between about 200 $m^2/g$ and about 700 $m^2/g$, between about 300 and about 350 $m^2/g$, between about 300 and about 400 $m^2/g$, between about 300 $m^2/g$ and about 450 $m^2/g$, between about 300 $m^2/g$ and about 500 $m^2/g$, between about 300 $m^2/g$ and about 600 $m^2/g$, between about 300 $m^2/g$ and about 700 $m^2/g$, between about 400 $m^2/g$ and about 700 $m^2/g$, between about 500 $m^2/g$ and about 700 $m^2/g$, or between about 600 $m^2/g$ and about 700 $m^2/g$. The surface area of the packing material particles may be determined using gas adsorption analysis techniques and calculations.

The packing material particles may have any suitable pore volume. According to certain embodiments, the packing material particles have a pore volume of at least about 0.6 mL/g, at least about 0.7 mL/g, at least about 0.8 mL/g, at least about 0.9 mL/g, at least about 1.0 mL/g, at least about 1.1 mL/g, at least about 1.2 mL/g, at least about 1.4 mL/g, at least about 1.6 mL/g, at least about 1.8 mL/g, or at least about 2.0 mL/g. In certain embodiments, the packing material particles have a pore volume or about 2.0 mL/g or less, about 1.8 mL/g or less, about 1.6 mL/g or less, about 1.4 mL/g or less, about 1.2 mL/g or less, about 1.1 mL/g or less, about 1.0 mL/g or less, about 0.9 mL/g or less, about 0.8 mL/g or less, about 0.7 mL/g or less, or about 0.6 mL/g or less. According to some embodiments, the packing material particles have a pore volume in a range between about 0.6 mL/g and about 0.8 mL/g, between about 0.6 mL/g and about 0.9 mL/g, between about 0.6 mL/g and about 1.0 mL/g, between about 0.6 mL/g and about 1.2 mL/g, between about 0.6 mL/g and about 1.4 mL/g, between about 0.6 mL/g and about 1.6 mL/g, between about 0.6 mL/g and about 1.8 mL/g, between about 0.6 mL/g and about 2.0 mL/g, between about 0.8 mL/g and about 1.0 mL/g, between about 0.8 mL/g and about 1.2 mL/g, between about 0.8 mL/g and about 1.4 mL/g, between about 0.8 mL/g and about 1.6 mL/g, between about 0.8 mL/g and about 1.8 mL/g, between about 0.8 mL/g and about 2.0 mL/g, between about 1.0 mL/g and about 1.4 mL/g, between about 1.0 mL/g and about 1.6 mL/g, between about 1.0 mL/g and about 1.8 mL/g, between about 1.0 mL/g and about 2.0 mL/g, between about 1.2 mL/g and about 2.0 mL/g, between about 1.4 mL/g and about 2.0 mL/g, between about 1.6 mL/g and about 2.0 mL/g, or between about 1.8 mL/g and about 2.0 mL/g. The pore volume of the packing material particles may be determined using gas adsorption analysis techniques and calculations. In some embodiments, the chromatography system comprises a mobile phase. The mobile phase generally refers to a fluid (e.g., a liquid, a supercritical fluid) that is configured to flow from a first end to a second end of a chromatography column through the stationary phase contained within the chromatography column. According to some embodiments, the mobile phase comprises carbon dioxide. The carbon dioxide may be supercritical $CO_2$ or liquid $CO_2$. Supercritical $CO_2$ and liquid $CO_2$ may both be desirable components of a mobile phase because they are generally chemically stable, non-toxic, non-flammable, inexpensive, and readily available. Moreover, since carbon dioxide is in gaseous phase at standard room temperature and pressure, any supercritical $CO_2$ or liquid $CO_2$ present in fractions collected from a chromatography column may simply evaporate under standard room temperature and pressure, obviating the need for further purification to remove the carbon dioxide from the collected fractions. As used herein, standard room temperature and pressure refers to a temperature of 20° C. and a pressure of 14.7 psia.

In certain embodiments, the mobile phase comprises supercritical carbon dioxide ($sCO_2$). Supercritical carbon dioxide generally refers to a fluid state of carbon dioxide, where the carbon dioxide is at or above its critical temperature (31.1° C.) and critical pressure (1,071 psia). Supercritical carbon dioxide may have certain properties that are similar to those of a liquid and certain other properties that are similar to those of a gas. For example, $sCO_2$ has a density that is close to that of a liquid solvent but a viscosity that is substantially lower than that of a typical liquid solvent. Accordingly, a mobile phase comprising $sCO_2$ may advantageously offer accurate and rapid separation of components within a mixture.

In some embodiments, the concentration of supercritical carbon dioxide in the mobile phase is relatively high. According to some embodiments, the concentration of supercritical carbon dioxide in the mobile phase is at least about 80 vol %, at least about 90 vol %, at least about 95 vol %, at least about 99 vol %, or about 100 vol %. The inventors have recognized and appreciated that a mobile phase comprising about 100% supercritical carbon dioxide (e.g., a mobile phase consisting of supercritical carbon dioxide) may be effective at separating one or more cannabis-derived compounds from one or more other components of a mixture. In certain embodiments, accordingly, the concentration of supercritical carbon dioxide in the mobile phase is 100% by volume. In some cases, a mobile phase comprising about 100 vol % of supercritical carbon dioxide may be referred to as "pure supercritical $CO_2$" or "pure $CO_2$." The concentration of a component (e.g., supercritical carbon dioxide) of the mobile phase may be measured according to any method known in the art. An exemplary method of measuring the concentration of a component of the mobile phase is gas chromatography (GC).

In some embodiments, the density of supercritical carbon dioxide in the mobile phase is relatively high. In some embodiments, the supercritical carbon dioxide has a density of at least about 400 kg/m³, at least about 500 kg/m³, at least about 600 kg/m³, at least about 700 kg/m³, at least about 800 kg/m³, at least about 900 kg/m³, at least about 1000 kg/m³, at least about 1100 kg/m³, or at least about 1200 kg/m³. In certain cases, the supercritical carbon dioxide in the mobile phase has a density in a range between about 400 kg/m³ and about 500 kg/m³, between about 400 kg/m³ and about 600 kg/m³, between about 400 kg/m³ and about 700 kg/m³, between about 400 kg/m³ and about 800 kg/m³, between about 400 kg/m³ and about 900 kg/m³, between about 400 kg/m³ and about 1000 kg/m³, between about 400 kg/m³ and about 1100 kg/m³, between about 400 kg/m³ and about 1200 kg/m³, between about 500 kg/m³ and about 600 kg/m³, between about 500 kg/m³ and about 700 kg/m³, between about 500 kg/m³ and about 800 kg/m³, between about 500 kg/m³ and about 900 kg/m³, between about 500 kg/m³ and about 1000 kg/m³, between about 500 kg/m³ and about 1100 kg/m³, between about 500 kg/m³ and about 1200 kg/m³, between about 600 kg/m³ and about 700 kg/m³, between about 600 kg/m³ and about 800 kg/m³, between about 600 kg/m³ and about 900 kg/m³, between about 600 kg/m³ and about 1000 kg/m³, between about 600 kg/m³ and about 1100 kg/m³, between about 600 kg/m³ and about 1200 kg/m³, between about 700 kg/m³ and about 800 kg/m³, between about 700 kg/m³ and about 900 kg/m³, between about 700 kg/m³ and about 1000 kg/m³, between about 700 kg/m³ and about 1100 kg/m³, between about 700 kg/m³ and about 1200 kg/m³, between about 800 kg/m³ and about 900 kg/m³, between about 800 kg/m³ and about 1000 kg/m³, between about 800 kg/m³ and about 1100 kg/m³, between about 800 kg/m³ and about 1200 kg/m³, between about 900 kg/m³ and about 1000 kg/m³, between about 900 kg/m³ and about 1100 kg/m³, between about 900 kg/m³ and about 1200 kg/m³, between about 1000 kg/m³ and about 1100 kg/m³, or between about 1000 kg/m³ and about 1200 kg/m³.

In some embodiments, the mobile phase comprises liquid carbon dioxide. Liquid $CO_2$ generally refers to a liquid state of carbon dioxide where its temperature is below its critical temperature (31.1° C.) and/or its pressure is below its critical pressure (1,071 psia). In some embodiments, the concentration of liquid $CO_2$ in the mobile phase is relatively high. According to some embodiments, the concentration of liquid $CO_2$ in the mobile phase is at least about 80 vol %, at least about 90 vol %, at least about 95 vol %, at least about 99 vol %, or about 100 vol %. The inventors have recognized and appreciated that a mobile phase comprising about 100% liquid $CO_2$ (e.g., a mobile phase consisting of liquid $CO_2$) may be effective at separating one or more cannabis-derived compounds from one or more other components of a mixture. In certain embodiments, accordingly, the concentration of liquid $CO_2$ in the mobile phase is 100% by volume. In some cases, a mobile phase comprising about 100 vol % of liquid carbon dioxide may be referred to as "pure liquid $CO_2$" or "pure $CO_2$."

In some embodiments, the density of liquid $CO_2$ in the mobile phase is relatively high. In some embodiments, the liquid $CO_2$ has a density of at least about 500 kg/m³, at least about 600 kg/m³, at least about 700 kg/m³, at least about 800 kg/m³, at least about 900 kg/m³, at least about 1000 kg/m³, at least about 1100 kg/m³, or at least about 1200 kg/m³. In certain cases, the liquid carbon dioxide has a density in a range between about 500 kg/m³ and about 700 kg/m³, between about 500 kg/m³ and about 800 kg/m³, between about 500 kg/m³ and about 900 kg/m³, between about 500 kg/m³ and about 1000 kg/m³, between about 500 kg/m³ and about 1100 kg/m³, between about 500 kg/m³ and about 1200 kg/m³, between about 600 kg/m³ and about 700 kg/m³, between about 600 kg/m³ and about 800 kg/m³, between about 600 kg/m³ and about 900 kg/m³, between about 600 kg/m³ and about 1000 kg/m³, between about 600 kg/m³ and about 1100 kg/m³, between about 600 kg/m³ and about 1200 kg/m³, between about 700 kg/m³ and about 800 kg/m³, between about 700 kg/m³ and about 900 kg/m³, between about 700 kg/m³ and about 1000 kg/m³, between about 700 kg/m³ and about 1100 kg/m³, between about 700 kg/m³ and about 1200 kg/m³, between about 800 kg/m³ and about 900 kg/m³, between about 800 kg/m³ and about 1000 kg/m³, between about 800 kg/m³ and about 1100 kg/m³, between about 800 kg/m³ and about 1200 kg/m³, between about 900 kg/m³ and about 1000 kg/m³, between about 900 kg/m³ and about 1100 kg/m³, between about 900 kg/m³ and about 1200 kg/m³, between about 1000 kg/m³ and about 1100 kg/m³, or between about 1000 kg/m³ and about 1200 kg/m³.

In some embodiments, the mobile phase is substantially free of a co-solvent that is in liquid phase at standard room temperature and pressure. In certain conventional chromatography methods, a liquid co-solvent (e.g., a polar liquid co-solvent) may be added to a mobile phase comprising carbon dioxide to enhance the solubility of polar compounds in the mobile phase. Non-limiting examples of co-solvents (e.g., polar co-solvents) that are in liquid phase at standard room temperature and pressure include methanol, ethanol, and acetonitrile. However, it may be undesirable to include such co-solvents in the liquid phase because these co-solvents are often flammable and toxic, and therefore unsuitable for human consumption or use, and because additional purification steps are typically required to remove them from collected fractions.

According to some embodiments, the concentration in the mobile phase of a co-solvent that is in liquid phase at standard room temperature and pressure is about 0.5 vol % or less, about 0.2 vol % or less, about 0.1 vol % or less, about 0.05 vol % or less, about 0.01 vol % or less, or about 0.0 vol %. In certain embodiments, the concentration in the mobile phase of a co-solvent that is in liquid phase at standard room temperature and pressure is in a range between about 0.0 vol % and about 0.01 vol %, between about 0.0 vol % and about 0.05 vol %, between about 0.0 vol % and about 0.1 vol %, between about 0.0 vol % and about 0.2 vol %, or between about 0.0 vol % and 0.5 vol %. In some cases, the mobile phase is considered to be substantially free of a co-solvent that is in liquid phase at standard room temperature and pressure if the concentration in the mobile phase of the co-solvent is about 0.5 vol % or less.

According to some embodiments, the total concentration in the mobile phase of any co-solvents is about 0.5 vol % or less, about 0.2 vol % or less, about 0.1 vol % or less, about 0.05 vol % or less, about 0.01 vol % or less, or about 0.0 vol %. In certain embodiments, the total concentration in the mobile phase of any co-solvents is in a range between about 0.0 vol % and about 0.01 vol %, between about 0.0 vol % and about 0.05 vol %, between about 0.0 vol % and about 0.1 vol %, between about 0.0 vol % and about 0.2 vol %, or between about 0.0 vol % and 0.5 vol %. In some cases, the mobile phase is considered to be substantially free of any co-solvents if the total concentration in the mobile phase of any co-solvents is about 0.5 vol % or less.

In certain embodiments, the mobile phase comprises a diluent. A diluent generally refers to a fluid that can be added to a solvent (e.g., carbon dioxide) of the mobile phase without substantially modifying the chromatographic properties (e.g., solubility of components to be separated) of the solvent. In some embodiments, the diluent is in gas or vapor phase at standard room temperature and pressure. A diluent that is in gas or vapor phase generally refers to a diluent that is not in liquid phase at standard room temperature and pressure.

The concentration in the mobile phase of a diluent (e.g., a diluent that is in gas or vapor phase at standard room temperature or pressure), if present, may be relatively low. According to some embodiments, the concentration in the mobile phase of a diluent may be about 50 vol % or less, about 40 vol % or less, about 30 vol % or less, about 20 vol % or less, about 10 vol % or less, about 5 vol % or less, about 2 vol % or less, about 1 vol % or less, about 0.5 vol % or less, about 0.1 vol % or less, about 0.05 vol % or less, about 0.01 vol % or less, or about 0 vol %. In certain embodiments, the concentration in the mobile phase of a diluent is in a range between about 0 vol % and about 0.01 vol %, between about 0 vol % and about 0.05 vol %, between about 0 vol % and about 0.1 vol %, between about 0 vol % and about 0.2 vol %, between about 0 vol % and 0.5 vol %, between about 0 vol % and about 1 vol %, between about 0 vol % and about 2 vol %, between about 0 vol % and about 5 vol %, between about 0 vol % and about 10 vol %, between about 0 vol % and about 20 vol %, between about 0 vol % and about 30 vol %, between about 0 vol % and about 40 vol %, between about 0 vol % and about 50 vol %, between about 1 vol % and about 2 vol %, between about 1 vol % and about 5 vol %, between about 1 vol % and about 10 vol %, between about 1 vol % and about 20 vol %, between about 1 vol % and about 30 vol %, between about 1 vol % and about 40 vol %, or between about 1 vol % and about 50 vol %.

In certain embodiments, the mobile phase comprises a co-solvent that is in gas or vapor phase at standard room temperature and pressure. A co-solvent that is in gas or vapor phase generally refers to a solvent that is not in liquid phase at standard room temperature and pressure. In some cases, the co-solvent may modify the chromatographic properties of another solvent (e.g., carbon dioxide) of the mobile phase. In certain cases, for example, the co-solvent may modify (e.g., increase) the solubility of certain compounds in the mobile phase. In some cases, it may be preferable to use a co-solvent that is in gas or vapor phase instead of liquid phase at standard room temperature and pressure, since such a co-solvent may be evaporated from a collected fraction under standard room temperature and pressure. Accordingly, no additional purification steps would be required to remove the co-solvent from collected fractions. Non-limiting examples of a suitable co-solvent that is in gaseous phase at standard room temperature and pressure include nitrous oxide, dimethyl ether, ethane, propane, butane, sulfur hexafluoride, and halocarbons.

The concentration in the mobile phase of a co-solvent that is in gas or vapor phase at standard room temperature and pressure may be relatively low. According to some embodiments, the concentration in the mobile phase of a co-solvent that is in gas or vapor phase at standard room temperature and pressure may be about 50 vol % or less, about 40 vol % or less, about 30 vol % or less, about 20 vol % or less, about 10 vol % or less, about 5 vol % or less, about 2 vol % or less, about 1 vol % or less, about 0.5 vol % or less, about 0.1 vol % or less, about 0.05 vol % or less, about 0.01 vol % or less, or about 0 vol %. In certain embodiments, the concentration in the mobile phase of a co-solvent that is in gas or vapor phase at standard room temperature and pressure is in a range between about 0 vol % and about 0.01 vol %, between about 0 vol % and about 0.05 vol %, between about 0 vol % and about 0.1 vol %, between about 0 vol % and about 0.2 vol %, between about 0 vol % and 0.5 vol %, between about 0 vol % and about 1 vol %, between about 0 vol % and about 2 vol %, between about 0 vol % and about 5 vol %, between about 0 vol % and about 10 vol %, between about 0 vol % and about 20 vol %, between about 0 vol % and about 30 vol %, between about 0 vol % and about 40 vol %, between about 0 vol % and about 50 vol %, between about 1 vol % and about 2 vol %, between about 1 vol % and about 5 vol %, between about 1 vol % and about 10 vol %, between about 1 vol % and about 20 vol %, between about 1 vol % and about 30 vol %, between about 1 vol % and about 40 vol %, or between about 1 vol % and about 50 vol %.

In some embodiments, the chromatography system comprises one or more instruments configured to analyze one or more fractions collected from the chromatography column. Non-limiting examples of suitable instruments include an ultraviolet-visible (UV-Vis) spectrophotometer, a mass spectrometer, and a flame ionization spectrometer. In some cases, the one or more instruments may generate data, such as a chromatogram comprising one or more peaks, for one or more of the collected fractions. In some cases, peaks within a chromatogram may be associated with different components of a mixture.

Certain embodiments described herein relate to chromatography methods for purifying a cannabis-derived compound from a mixture. In some embodiments, the method comprises injecting a mixture comprising a first component and a second component into a chromatography column containing a stationary phase. The injecting step may occur over a single defined time interval or over multiple time intervals. In certain embodiments, the mixture is injected into the column substantially continuously.

In some embodiments, the method comprises transporting the mixture through the chromatography column. The mixture may be transported within a mobile phase from a first end to a second end of the chromatography column, and the mixture may be in contact with the stationary phase as it is transported through the chromatography column. In certain embodiments, a first component and a second component of the mixture interact with the stationary phase and/or the mobile phase to different degrees such that the first component is at least partially separated from the second component within the column.

In some embodiments, the first component and the second component of the mixture are each transported within the mobile phase substantially continuously from a first end to a second end of the chromatography column. As used herein, a component of the mixture is transported "substantially continuously" if the component travels through the column with a non-zero velocity whenever the mobile phase is flowing at a non-zero flow rate. Accordingly, if transport of the component is temporarily stopped (e.g., the component has a velocity of zero) due to flow of the mobile phase being temporarily stopped (e.g., the mobile phase has a flow rate of zero), but the component has a non-zero velocity whenever the mobile phase is flowing, the component will still be considered to be transported "substantially continuously." However, if transport of the component is stopped (e.g., due to the component binding to the stationary phase) while the mobile phase continues to flow at a non-zero flow rate, the component will not be considered to be transported "substantially continuously" from a first end to a second end of the chromatography column.

In some embodiments, the transporting step is performed at a temperature at or above the critical temperature of carbon dioxide (31.1° C.). According to certain embodiments, the transporting step is performed at a temperature of at least about 31° C., at least about 35° C., at least about 40° C., at least about 45° C., at least about 50° C., at least about 55° C., at least about 60° C., at least about 65° C., or at least about 70° C. In some cases, the transporting step is performed at a temperature in a range between about 31° C. and about 40° C., between about 31° C. and about 45° C., between about 31° C. and about 50° C., between about 31° C. and about 55° C., between about 31° C. and about 60° C., between about 31° C. and about 65° C., between about 31° C. and about 70° C., between about 35° C. and about 40° C., between about 35° C. and about 45° C., between about 35° C. and about 50° C., between about 35° C. and about 55° C., between about 35° C. and about 60° C., between about 35° C. and about 65° C., between about 35° C. and about 70° C., between about 40° C. and about 45° C., between about 40° C. and about 50° C., between about 40° C. and about 55° C., between about 40° C. and about 60° C., between about 40° C. and about 65° C., between about 40° C. and about 70° C., between about 45° C. and about 50° C., between about 45° C. and about 55° C., between about 45° C. and about 60° C., between about 45° C. and about 65° C., between about 45° C. and about 70° C., between about 50° C. and about 55° C., between about 50° C. and about 60° C., between about 50° C. and about 65° C., between about 50° C. and about 70° C., between about 55° C. and about 60° C., between about 55° C. and about 65° C., between about 55° C. and about 70° C., between about 60° C. and about 65° C., between about 60° C. and about 70° C., or between about 65° C. and about 70° C. In these embodiments, the mobile phase may comprise supercritical $CO_2$ or liquid $CO_2$.

In some embodiments, the transporting step is performed at a temperature below the critical temperature of carbon dioxide (31.1° C.). According to certain embodiments, the transporting step is performed at a temperature of about 31° C. or less, about 30° C. or less, about 25° C. or less, about 20° C. or less, about 15° C. or less, about 10° C. or less, about 5° C. or less, about 0° C. or less, about −5° C. or less, or about −10° C. or less. In some cases, the transporting step is performed at a temperature in a range between about −10° C. and about 0° C., between about −10° C. and about 5° C., between about −10° C. and about 10° C., between about −10° C. and about 15° C., between about −10° C. and about 20° C., between about −10° C. and about 25° C., between about −10° C. and about 30° C., between about −10° C. and about 31° C., between about 0° C. and about 5° C., between about 0° C. and about 10° C., between about 0° C. and about 15° C., between about 0° C. and about 20° C., between about 0° C. and about 25° C., between about 0° C. and about 30° C., or between about 0° C. and about 31° C. In these embodiments, the mobile phase may comprise liquid $CO_2$.

In some embodiments, the transporting step is performed at a pressure at or above the critical pressure of carbon dioxide (1,071 psia). Unless otherwise noted, all pressures given in units of pounds per square inch (psi) refer to gauge pressure (psig) measured relative to atmospheric pressure. In some embodiments, the transporting step is performed at a pressure of at least about 1,071 psi, at least about 1085.7 psi, at least about 1,100 psi, at least about 1,500 psi, at least about 2,000 psi, at least about 2,500 psi, at least about 3,000 psi, at least about 3,500 psi, at least about 4,000 psi, at least about 4,500 psi, at least about 5,000 psi, at least about 5,500 psi, at least about 6,000 psi, at least about 6,500 psi, at least about 7,000 psi, at least about 7,500 psi, at least about 8,000 psi, at least about 8,500 psi, at least about 9,000 psi, at least about 9,500 psi, at least about 10,000 psi, at least about 15,000 psi, at least about 20,000 psi, at least about 25,000 psi, or at least about 30,000 psi. In some embodiments, the transporting step is performed at a pressure in a range between about 1,071 psi and about 2,000 psi, between about 1,071 psi and about 3,000 psi, between about 1,071 psi and about 4,000 psi, between about 1,071 psi and about 5,000 psi, between about 1,071 psi and about 6,000 psi, between about 1,071 psi and about 7,000 psi, between about 1,071 psi and about 8,000 psi, between about 1,071 psi and about 9,000 psi, between about 1,071 psi and about 10,000 psi, between about 1,071 psi and about 15,000 psi, between about 1,071 psi and about 20,000 psi, between about 1,071 psi and about 25,000 psi, between about 1,071 psi and about 30,000 psi, between about 1085.7 psi and about 2,000 psi, between about 1085.7 psi and about 3,000 psi, between about 1085.7 psi and about 4,000 psi, between about 1085.7 psi and about 5,000 psi, between about 1085.7 psi and about 6,000 psi, between about 1085.7 psi and about 7,000 psi, between about 1085.7 psi and about 8,000 psi, between about 1085.7 psi and about 9,000 psi, between about 1085.7 psi and about 10,000 psi, between about 1085.7 psi and about 15,000 psi, between about 1085.7 psi and about 20,000 psi, between about 1085.7 psi and about 25,000 psi, between about 1085.7 psi and about 30,000 psi, between about 1,100 psi and about 2,000 psi, between about 1,100 psi and about 3,000 psi, between about 1,100 psi and about 4,000 psi, between about 1,100 psi and about 5,000 psi, between about 1,100 psi and about 6,000 psi, between about 1,100 psi and about 7,000 psi, between about 1,100 psi and about 8,000 psi, between about 1,100 psi and about 9,000 psi, between about 1,100 psi and about 10,000 psi, between about 1,100 psi and about 15,000 psi, between about 1,100 psi and about 20,000 psi, between about 1,100 psi and about 25,000 psi, between about 1,100 psi and about 30,000 psi, between about 2,000 psi and about 3,000 psi, between about 2,000 psi and about 4,000 psi, between about 2,000 psi and about 5,000 psi, between about 2,000 psi and about 6,000 psi, between about 2,000 psi and about 7,000 psi, between about 2,000 psi and about 8,000 psi, between about 2,000 psi and about 9,000 psi, between about 2,000 psi and about 10,000 psi, between about 2,000 psi and about 15,000 psi, between about 2,000 psi and about 20,000 psi, between about 2,000 psi and about 25,000 psi, between about 2,000 psi and about 30,000 psi, between about 3,000 psi and about 5,000 psi, between about 3,000 psi and about 6,000 psi, between about 3,000 psi and about 7,000 psi, between about 3,000 psi and about 8,000 psi, between about 3,000 psi and about 9,000 psi, between about 3,000 psi and about 10,000 psi, between about 3,000 psi and about 15,000 psi, between about 3,000 psi and about 20,000 psi, between about 3,000 psi and about 25,000 psi, between about 3,000 psi and about 30,000 psi, between about 5,000 psi and about 7,000 psi, between about 5,000 psi and about 8,000 psi, between about 5,000 psi and about 9,000 psi, between about 5,000 psi and about 10,000 psi, between about 5,000 psi and about 15,000 psi, between about 5,000 psi and about 20,000 psi, between about 5,000 psi and about 25,000 psi, between about 5,000 psi and about 30,000 psi, between about 10,000 psi and about 15,000 psi, between about 10,000 psi and about 20,000 psi, between about 10,000 psi and about 25,000 psi, between about 10,000 psi and about 30,000 psi, between about 15,000 psi and about 20,000 psi, between about 15,000 psi and about 25,000 psi, between about 15,000 psi and about 30,000 psi, between about 20,000 psi and about 25,000 psi, or between about 20,000 psi and about 30,000 psi. The pressure at which the transporting step is performed may be measured using any suitable pressure gauge. In these embodiments, the mobile phase may comprise supercritical $CO_2$ or liquid $CO_2$.

In some embodiments, the transporting step is performed at a pressure below the critical pressure of carbon dioxide (1,071 psia). In some embodiments, the transporting step is performed at a pressure of about 1,100 psi or less, about 1085.7 psi or less, about 1,071 psi or less, about 1,000 psi or less, about 900 psi or less, about 800 psi or less, about 700 psi or less, about 600 psi or less, or about 500 psi or less. In some embodiments, the transporting step is performed at a pressure in a range between about 500 psi and about 600 psi, about 500 psi and about 700 psi, about 500 psi and about 800 psi, about 500 psi and about 900 psi, about 500 psi and about 1,000 psi, about 500 psi and about 1,071 psi, about 500 psi and about 1085.7 psi, or about 500 psi and about 1,100 psi. In these embodiments, the mobile phase may comprise liquid $CO_2$.

In some embodiments, the transporting step is performed at a pressure in a range between about 500 psi and about 2,000 psi, between about 500 psi and about 3,000 psi, between about 500 psi and about 4,000 psi, between about 500 psi and about 5,000 psi, between about 500 psi and about 6,000 psi, between about 500 psi and about 7,000 psi, between about 500 psi and about 8,000 psi, between about 500 psi and about 9,000 psi, between about 500 psi and about 10,000 psi, between about 500 psi and about 15,000 psi, between about 500 psi and about 20,000 psi, between about 500 psi and about 25,000 psi, or between about 500 psi and about 30,000 psi.

In some embodiments, the transporting step is performed under substantially constant pressure. In certain other embodiments, at least a portion of the transporting step may be performed under varying pressure conditions. For example, pressure may be increased or decreased during at least a portion of the transporting step. In certain cases, pressure may be changed (e.g., increased or decreased) after one or more desired components of a mixture have been transported through the column and have been collected as fractions.

In some embodiments, the transporting step is performed at a temperature above the critical temperature of carbon dioxide and a pressure above the critical pressure of carbon dioxide. In certain embodiments, the transporting step may be performed at a temperature of at least about 31° C. and a pressure of at least about 1,071 psi, a temperature of at least about 31° C. and a pressure of at least about 1085.7 psi, a temperature of at least about 31° C. and a pressure of at least about 1,100 psi, a temperature of at least about 31° C. and a pressure of at least about 2,000 psi, a temperature of at least about 31° C. and a pressure of at least about 5,000 psi, a temperature of at least about 31° C. and a pressure of at least about 10,000 psi, a temperature of at least about 40° C. and a pressure of at least about 1,071 psi, a temperature of at least about 40° C. and a pressure of at least about 1085.7 psi, a temperature of at least about 40° C. and a pressure of at least about 1,100 psi, a temperature of at least about 40° C. and a pressure of at least about 2,000 psi, a temperature of at least about 40° C. and a pressure of at least about 5,000 psi, or a temperature of at least about 40° C. and a pressure of at least about 10,000 psi. As illustrative, non-limiting examples, the transporting step may be performed at a temperature in a range between about 31° C. and about 70° C. and a pressure in a range between about 1,071 psi and about 10,000 psi, at a temperature in a range between about 31° C. and about 70° C. and a pressure in a range between about 1,071 psi and about 20,000 psi, at a temperature in a range between about 31° C. and about 70° C. and a pressure in a range between about 1,071 psi and about 30,000 psi, at a temperature in a range between about 31° C. and about 70° C. and a pressure in a range between about 1085.7 psi and about 10,000 psi, at a temperature in a range between about 31° C. and about 70° C. and a pressure in a range between about 1085.7 psi and about 20,000 psi, at a temperature in a range between about 31° C. and about 70° C. and a pressure in a range between about 1085.7 psi and about 30,000 psi, at a temperature in a range between about 31° C. and about 70° C. and a pressure in a range between about 1,100 psi and about 10,000 psi, at a temperature in a range between about 31° C. and about 70° C. and a pressure in a range between about 1,100 psi and about 20,000 psi, at a temperature in a range between about 31° C. and about 70° C. and a pressure in a range between about 1,100 psi and about 30,000 psi, at a temperature in a range between about 40° C. and about 70° C. and a pressure in a range between about 1,071 psi and about 10,000 psi, at a temperature in a range between about 40° C. and about 70° C. and a pressure in a range between about 1,071 psi and about 20,000 psi, at a temperature in a range between about 40° C. and about 70° C. and a pressure in a range between about 1,071 psi and about 30,000 psi, at a temperature in a range between about 40° C. and about 70° C. and a pressure in a range between about 1087.5 psi and about 10,000 psi, at a temperature in a range between about 40° C. and about 70° C. and a pressure in a range between about 1087.5 psi and about 20,000 psi, at a temperature in a range between about 40° C. and about 70° C. and a pressure in a range between about 1087.5 psi and about 30,000 psi, at a temperature in a range between about 40° C. and about 70° C. and a pressure in a range between about 1,100 psi and about 10,000 psi, at a temperature in a range between about 40° C. and about 70° C. and a pressure in a range between about 1,100 psi and about 20,000 psi, at a temperature in a range between about 40° C. and about 70° C. and a pressure in a range between about 1,100 psi and about 30,000 psi, at a temperature in a range between about 40° C. and about 70° C. and a pressure in a range between about 2,000 psi and about 10,000 psi, at a temperature in a range between about 40° C. and about 70° C. and a pressure in a range between about 2,000 psi and about 20,000 psi, or at a temperature in a range between about 40° C. and about 70° C. and a pressure in a range between about 2,000 psi and about 30,000 psi. In certain of these embodiments, the mobile phase comprises supercritical $CO_2$.

In some embodiments, the transporting step is performed at a temperature below the critical temperature of carbon dioxide and/or a pressure below the critical pressure of carbon dioxide. In certain embodiments, the transporting step may be performed at a temperature of about 31° C. or less and/or a pressure of about 1,085.7 psi or less, a temperature of about 31° C. or less and/or a pressure of about 1,071 psi or less, a temperature of about 31° C. or less and/or a pressure of about 1,000 psi or less, a temperature of about 31° C. or less and/or a pressure of about 500 psi or less, a temperature of about 30° C. or less and/or a pressure of about 1,085.7 psi or less, a temperature of about 30° C. or less and/or a pressure of about 1,071 psi or less, a temperature of about 30° C. or less and/or a pressure of about 1,000 psi or less, a temperature of about 30° C. or less and/or a pressure of about 500 psi or less, a temperature of about 0° C. or less and/or a pressure of about 1,085.7 psi or less, a temperature of about 0° C. or less and/or a pressure of about 1,071 psi or less, a temperature of about 0° C. or less and/or a pressure of about 1,000 psi or less, or a temperature of about 0° C. or less and/or a pressure of about 500 psi or less. In some embodiments, the transporting step is performed at a temperature below the critical temperature of carbon dioxide and a pressure above the critical pressure of carbon dioxide. In certain instances, the transporting step may be performed at a temperature of about 31° C. or less and a pressure of at least about 1,071 psi, a temperature of about 31° C. or less and a pressure of at least about 1,085.7 psi, a temperature of about 31° C. or less and a pressure of at least about 1,100 psi, a temperature of about 31° C. or less and a pressure of at least about 2,000 psi, a temperature of about 31° C. or less and a pressure of at least about 5,000 psi, a temperature of about 31° C. or less and a pressure of at least about 10,000 psi, a temperature of about 30° C. or less and a pressure of at least about 1,071 psi, a temperature of about 30° C. or less and a pressure of at least about 1,085.7 psi, a temperature of about 30° C. or less and a pressure of at least about 1,100 psi, a temperature of about 30° C. or less and a pressure of at least about 2,000 psi, a temperature of about 30° C. or less and a pressure of at least about 5,000 psi, or a temperature of about 30° C. or less and a pressure of at least about 10,000 psi. As illustrative, non-limiting examples, the transporting step may be performed at a temperature in a range between about 0° C. and about 30° C. and a pressure in a range between about 500 psi and about 1,000 psi, at a temperature in a range between about 0° C. and about 30° C. and a pressure in a range between about 500 psi and about 1,071 psi, at a temperature in a range between about 0° C. and about 30° C. and a pressure in a range between about 500 psi and about 1,085.7 psi, at a temperature in a range between about 0° C. and about 30° C. and a pressure in a range between about 500 psi and about 1,100 psi, at a temperature in a range between about 0° C. and about 30° C. and a pressure in a range between about 500 psi and about 2,000 psi, at a temperature in a range between about 0° C. and about 30° C. and a pressure in a range between about 500 psi and about 5,000 psi, at a temperature in a range between about 0° C. and about 30° C. and a pressure in a range between about 500 psi and about 10,000 psi, or at a temperature in a range between about 0° C. and about 31° C. and a pressure in a range between about 500 psi and about 10,000 psi. In certain of these embodiments, the mobile phase comprises liquid $CO_2$.

During the transporting step, the mobile phase may flow through the column at any suitable flow rate. In certain embodiments, the flow rate of the mobile phase during the transporting step is at least about 1 mL/min, at least about 2 mL/min, at least about 5 mL/min, at least about 10 mL/min, at least about 20 mL/min, at least about 50 mL/min, at least about 100 mL/min, at least about 500 mL/min, at least about 1,000 mL/min, at least about 5,000 mL/min, at least about 10,000 mL/min, at least about 50,000 mL/min, or at least about 100,000 mL/min. In some embodiments, the flow rate of the mobile phase during the transporting step is in a range between about 1 mL/min and about 5 mL/min, between about 1 mL/min and about 10 mL/min, between about 1 mL/min and about 50 mL/min, between about 1 mL/min and about 100 mL/min, between about 1 mL/min and about 500 mL/min, between about 1 mL/min and about 1,000 mL/min, between about 1 mL/min and about 5,000 mL/min, between about 1 mL/min and about 10,000 mL/min, between about 1 mL/min and about 50,000 mL/min, between about 1 mL/min and about 100,000 mL/min, between about 10 mL/min and about 50 mL/min, between about 10 mL/min and about 100 mL/min, between about 10 mL/min and about 500 mL/min, between about 10 mL/min and about 1,000 mL/min, between about 10 mL/min and about 5,000 mL/min, between about 10 mL/min and about 10,000 mL/min, between about 10 mL/min and about 50,000 mL/min, between about 10 mL/min and about 100,000 mL/min, between about 100 mL/min and about 500 mL/min, between about 100 mL/min and about 1,000 mL/min, between about 100 mL/min and about 5,000 mL/min, between about 100 mL/min and about 10,000 mL/min, between about 100 mL/min and about 50,000 mL/min, between about 100 mL/min and about 100,000 mL/min, between about 1,000 mL/min and about 5,000 mL/min, between about 1,000 mL/min and about 10,000 mL/min, between about 1,000 mL/min and about 50,000 mL/min, between about 1,000 mL/min and about 100,000 mL/min, between about 10,000 mL/min and about 100,000 mL/min, or between about 50,000 mL/min and about 100,000 mL/min. The flow rate of the mobile phase may be measured according to any method known in the art. In an exemplary method, the flow rate of the mobile phase may be measured using a flow rate meter.

In some embodiments, the chromatography method further comprises collecting a first fraction of the mobile phase over a first time interval. In certain embodiments, the first fraction comprises the first component of the mixture. In some instances, the first fraction comprises a single fraction collected from the chromatography column. In other instances, the first fraction comprises a plurality of fractions, each fraction comprising the first component of the mixture. As an illustrative, non-limiting example, it may be determined through one or more analytical techniques that two or more fractions (e.g., the fifth fraction through the tenth fraction collected) contain the first component of the mixture. In some cases, the two or more fractions containing the first component of the mixture may be combined and collectively referred to as the first fraction.

In some embodiments, the concentration of the first component in the first fraction is relatively high. According to certain embodiments, the concentration of the first component in the first fraction is at least about 10 wt %, at least about 20 wt %, at least about 30 wt %, at least about 40 wt %, at least about 50 wt %, at least about 60 wt %, at least about 70 wt %, at least about 80 wt %, at least about 85 wt %, at least about 90 wt %, at least about 95 wt %, at least about 99 wt %, at least about 99.99 wt %, or at least about 99.9999 wt %. In some embodiments, the concentration of the first component in the first fraction is in a range between about 10 wt % and about 50 wt %, between about 10 wt % and about 60 wt %, between about 10 wt % and about 70 wt %, between about 10 wt % and about 80 wt %, between about 10 wt % and about 90 wt %, between about 10 wt % and about 95 wt %, between about 10 wt % and about 99 wt %, between about 10 wt % and about 100 wt %, between about 20 wt % and about 50 wt %, between about 20 wt % and about 60 wt %, between about 20 wt % and about 70 wt %, between about 20 wt % and about 80 wt %, between about 20 wt % and about 90 wt %, between about 20 wt % and about 95 wt %, between about 20 wt % and about 99 wt %, between about 20 wt % and about 100 wt %, between about 50 wt % and about 60 wt %, between about 50 wt % and about 70 wt %, between about 50 wt % and about 80 wt %, between about 50 wt % and about 90 wt %, between about 50 wt % and about 95 wt %, between about 50 wt % and about 99 wt %, between about 50 wt % and about 100 wt %, between about 70 wt % and about 80 wt %, between about 70 wt % and about 90 wt %, between about 70 wt % and about 95 wt %, between about 70 wt % and about 99 wt %, between about 70 wt % and about 100 wt %, between about 80 wt % and about 90 wt %, between about 80 wt % and about 95 wt %, between about 80 wt % and about 99 wt %, between about 80 wt % and about 100 wt %, between about 90 wt % and about 95 wt %, between about 90 wt % and about 99 wt %, between about 90 wt % and about 99.99 wt %, between about 90 wt % and about 99.9999 wt %, or between about 90 wt % and about 100 wt %. A suitable method for measuring a concentration of a component in a fraction is by analyzing a sample of the fraction by liquid chromatography-mass spectrometry (LC-MS).

In some embodiments, the concentration of the second component in the first fraction is relatively low. According to certain embodiments, the concentration of the second component in the first fraction is about 5 wt % or less, about 2 wt % or less, about 1 wt % or less, about 0.5 wt % or less, about 0.2 wt % or less, about 0.1 wt % or less, about 0.05 wt % or less, about 0.01 wt % or less, about 0.005 wt % or less, about 0.001 wt % or less, or about 0 wt %. In some embodiments, the concentration of the second component in the first fraction is in a range between about 0 wt % and about 0.1 wt %, between about 0 wt % and about 0.2 wt %, between about 0 wt % and about 0.5 wt %, between about 0 wt % and about 1 wt %, between about 0 wt % and about 2 wt %, or between about 0 wt % and about 5 wt %. In some embodiments, the first fraction is substantially free of the second component. The first fraction may be considered to be substantially free of the second component if the concentration of the second component in the first fraction is about 5 wt % or less.

In some embodiments, the total concentration of all components other than the first component in the first fraction is relatively low. In certain cases, the total concentration of all components other than the first component in the first fraction is about 5 wt % or less, about 2 wt % or less, about 1 wt % or less, about 0.5 wt % or less, about 0.2 wt % or less, about 0.1 wt % or less, about 0.05 wt % or less, about 0.01 wt % or less, about 0.005 wt % or less, about 0.001 wt % or less, or about 0 wt %. In some embodiments, the total concentration of all components other than the first component in the first fraction is in a range between about 0 wt % and about 0.1 wt %, between about 0 wt % and about 0.2 wt %, between about 0 wt % and about 0.5 wt %, between about 0 wt % and about 1 wt %, between about 0 wt % and about 2 wt %, or between about 0 wt % and about 5 wt %. In some embodiments, the first fraction is substantially free of all components other than the first component. The first fraction may be considered to be substantially free of all components other than the first component if the total concentration of all other components in the first fraction is about 5 wt % or less.

In some embodiments, the chromatography method further comprises collecting a second fraction of the mobile phase over a second time interval that is different from and does not overlap the first time interval. In certain embodiments, the second fraction comprises the second component of the mixture. In some instances, the second fraction comprises a single fraction collected from the chromatography column. In other instances, the second fraction comprises a plurality of fractions, each fraction comprising the second component of the mixture. As an illustrative, non-limiting example, it may be determined through one or more analytical techniques that two or more fractions (e.g., the twelfth fraction through the fifteenth fraction collected) contain the second component of the mixture. In some cases, the two or more fractions containing the second component of the mixture may be combined and collectively referred to as the second fraction. The second fraction may be collected before or after the first fraction.

In some embodiments, the concentration of the second component in the second fraction is relatively high. According to certain embodiments, the concentration of the second component in the second fraction is at least about 10 wt %, at least about 20 wt %, at least about 30 wt %, at least about 40 wt %, at least about 50 wt %, at least about 60 wt %, at least about 70 wt %, at least about 80 wt %, at least about 85 wt %, at least about 90 wt %, at least about 95 wt %, at least about 99 wt %, at least about 99.99 wt %, or at least about 99.9999 wt %. In some embodiments, the concentration of the second component in the second fraction is in a range between about 10 wt % and about 50 wt %, between about 10 wt % and about 60 wt %, between about 10 wt % and about 70 wt %, between about 10 wt % and about 80 wt %, between about 10 wt % and about 90 wt %, between about 10 wt % and about 95 wt %, between about 10 wt % and about 99 wt %, between about 10 wt % and about 100 wt %, between about 20 wt % and about 50 wt %, between about 20 wt % and about 60 wt %, between about 20 wt % and about 70 wt %, between about 20 wt % and about 80 wt %, between about 20 wt % and about 90 wt %, between about 20 wt % and about 95 wt %, between about 20 wt % and about 99 wt %, between about 20 wt % and about 100 wt %, between about 50 wt % and about 60 wt %, between about 50 wt % and about 70 wt %, between about 50 wt % and about 80 wt %, between about 50 wt % and about 90 wt %, between about 50 wt % and about 95 wt %, between about 50 wt % and about 99 wt %, between about 50 wt % and about 100 wt %, between about 70 wt % and about 80 wt %, between about 70 wt % and about 90 wt %, between about 70 wt % and about 95 wt %, between about 70 wt % and about 99 wt %, between about 70 wt % and about 100 wt %, between about 80 wt % and about 90 wt %, between about 80 wt % and about 95 wt %, between about 80 wt % and about 99 wt %, between about 80 wt % and about 100 wt %, between about 90 wt % and about 95 wt %, between about 90 wt % and about 99 wt %, between about 90 wt % and about 99.99 wt %, between about 90 wt % and about 99.9999 wt %, or between about 90 wt % and about 100 wt %.

In some embodiments, the concentration of the first component in the second fraction is relatively low. According to certain embodiments, the concentration of the first component in the second fraction is about 5 wt % or less, about 2 wt % or less, about 1 wt % or less, about 0.5 wt % or less, about 0.2 wt % or less, about 0.1 wt % or less, about 0.05 wt % or less, about 0.01 wt % or less, about 0.005 wt % or less, about 0.001 wt % or less, or about 0 wt %. In some embodiments, the concentration of the first component in the second fraction is in a range between about 0 wt % and about 0.1 wt %, between about 0 wt % and about 0.2 wt %, between about 0 wt % and about 0.5 wt %, between about 0 wt % and about 1 wt %, between about 0 wt % and about 2 wt %, or between about 0 wt % and about 5 wt %. In some embodiments, the second fraction is substantially free of the first component. The second fraction may be considered to be substantially free of the first component if the concentration of the first component in the second fraction is about 5 wt % or less.

In some embodiments, the total concentration of all components other than the second component in the second fraction is relatively low. In certain cases, the total concentration of all components other than the second component in the second fraction is about 5 wt % or less, about 2 wt % or less, about 1 wt % or less, about 0.5 wt % or less, about 0.2 wt % or less, about 0.1 wt % or less, about 0.05 wt % or less, about 0.01 wt % or less, about 0.005 wt % or less, about 0.001 wt % or less, or about 0 wt %. In some embodiments, the total concentration of all components other than the second component in the second fraction is in a range between about 0 wt % and about 0.1 wt %, between about 0 wt % and about 0.2 wt %, between about 0 wt % and about 0.5 wt %, between about 0 wt % and about 1 wt %, between about 0 wt % and about 2 wt %, or between about 0 wt % and about 5 wt %. In some embodiments, the second fraction is substantially free of all components other than the second component. The second fraction may be considered to be substantially free of all components other than the second component if the total concentration of all other components in the second fraction is about 5 wt % or less.

In some embodiments, the chromatography method further comprises collecting a third fraction of the mobile phase over a third time interval that is different from and does not overlap the first time interval and the second time interval. In certain embodiments, the third fraction comprises the third component of the mixture. In some instances, the third fraction comprises a single fraction collected from the chromatography column. In other instances, the third fraction comprises a plurality of fractions, each fraction comprising the third component of the mixture. As an illustrative, non-limiting example, it may be determined through one or more analytical techniques that two or more fractions (e.g., the eighteenth fraction through the twenty-third fraction collected) contain the third component of the mixture. In some cases, the two or more fractions containing the third component of the mixture may be combined and collectively referred to as the third fraction. The third fraction may be collected before or after the first fraction and the second fraction.

In some embodiments, the concentration of the third component in the third fraction is relatively high. According to certain embodiments, the concentration of the third component in the third fraction is at least about 10 wt %, at least about 20 wt %, at least about 30 wt %, at least about 40 wt %, at least about 50 wt %, at least about 60 wt %, at least about 70 wt %, at least about 80 wt %, at least about 85 wt %, at least about 90 wt %, at least about 95 wt %, at least about 99 wt %, at least about 99.99 wt %, or at least about 99.9999 wt %. In some embodiments, the concentration of the third component in the third fraction is in a range between about 10 wt % and about 50 wt %, between about 10 wt % and about 60 wt %, between about 10 wt % and about 70 wt %, between about 10 wt % and about 80 wt %, between about 10 wt % and about 90 wt %, between about 10 wt % and about 95 wt %, between about 10 wt % and about 99 wt %, between about 10 wt % and about 100 wt %, between about 20 wt % and about 50 wt %, between about 20 wt % and about 60 wt %, between about 20 wt % and about 70 wt %, between about 20 wt % and about 80 wt %, between about 20 wt % and about 90 wt %, between about 20 wt % and about 95 wt %, between about 20 wt % and about 99 wt %, between about 20 wt % and about 100 wt %, between about 50 wt % and about 60 wt %, between about 50 wt % and about 70 wt %, between about 50 wt % and about 80 wt %, between about 50 wt % and about 90 wt %, between about 50 wt % and about 95 wt %, between about 50 wt % and about 99 wt %, between about 50 wt % and about 100 wt %, between about 70 wt % and about 80 wt %, between about 70 wt % and about 90 wt %, between about 70 wt % and about 95 wt %, between about 70 wt % and about 99 wt %, between about 70 wt % and about 100 wt %, between about 80 wt % and about 90 wt %, between about 80 wt % and about 95 wt %, between about 80 wt % and about 99 wt %, between about 80 wt % and about 100 wt %, between about 90 wt % and about 95 wt %, between about 90 wt % and about 99 wt %, between about 90 wt % and about 99.99 wt %, between about 90 wt % and about 99.9999 wt %, or between about 90 wt % and about 100 wt %.

In some embodiments, the concentration of the first component and/or the second component in the third fraction is relatively low. According to certain embodiments, the concentration of the first component and/or the second component in the third fraction is about 5 wt % or less, about 2 wt % or less, about 1 wt % or less, about 0.5 wt % or less, about 0.2 wt % or less, about 0.1 wt % or less, about 0.05 wt % or less, about 0.01 wt % or less, about 0.005 wt % or less, about 0.001 wt % or less, or about 0 wt %. In some embodiments, the concentration of the first component and/or the second component in the third fraction is in a range between about 0 wt % and about 0.1 wt %, between about 0 wt % and about 0.2 wt %, between about 0 wt % and about 0.5 wt %, between about 0 wt % and about 1 wt %, between about 0 wt % and about 2 wt %, or between about 0 wt % and about 5 wt %. In some embodiments, the third fraction is substantially free of the first component and/or the second component. The third fraction may be considered to be substantially free of the first component and/or the second component if the concentration of the first component and/or the second component in the third fraction is about 5 wt % or less.

In some embodiments, the total concentration of all components other than the third component in the third fraction is relatively low. In certain cases, the total concentration of all components other than the third component in the third fraction is about 5 wt % or less, about 2 wt % or less, about 1 wt % or less, about 0.5 wt % or less, about 0.2 wt % or less, about 0.1 wt % or less, about 0.05 wt % or less, about 0.01 wt % or less, about 0.005 wt % or less, about 0.001 wt % or less, or about 0 wt %. In some embodiments, the total concentration of all components other than the third component in the third fraction is in a range between about 0 wt % and about 0.1 wt %, between about 0 wt % and about 0.2 wt %, between about 0 wt % and about 0.5 wt %, between about 0 wt % and about 1 wt %, between about 0 wt % and about 2 wt %, or between about 0 wt % and about 5 wt %. In some embodiments, the third fraction is substantially free of all components other than the third component. The third fraction may be considered to be substantially free of all components other than the third component if the total concentration of all other components in the third fraction is about 5 wt % or less.

In some embodiments, the chromatography method further comprises collecting any number of additional fractions comprising additional components of the mixture. According to certain embodiments, each additional fraction may have a relatively high concentration of at least one component of the mixture. In some cases, each additional fraction may have a relatively low concentration of at least one other component of the mixture (e.g., the first component, the second component, the third component). In some cases, each additional fraction may have a relatively low total concentration of all other components of the mixture.

In some embodiments, the method further comprises analyzing one or more fractions (e.g., the first fraction, the second fraction, the third fraction) collected from the chromatography column. The one or more fractions may be analyzed according to any suitable method known in the art. In some cases, the fractions may be analyzed using a UV-Vis spectrophotometer, a mass spectrometer, and/or a flame ionization spectrometer. In some cases, a chromatogram may be produced for one or more of the collected fractions.

In some embodiments, the method further comprises processing one or more fractions to render them suitable for human consumption or use. According to certain embodiments, the method comprises forming a product suitable for oral administration to humans. In certain cases, for example, the method further comprises forming a tablet and/or capsule comprising at least a portion of one or more fractions (e.g., the first fraction, the second fraction) collected from the chromatography column. In some embodiments, at least a portion of the one or more fractions may be added to a food item that is suitable for human consumption. According to certain other embodiments, the method comprises forming a product suitable for inhalation by humans. In some embodiments, the method comprises forming a product suitable for topical application (e.g., a topical cream).

The following examples are intended to illustrate certain embodiments of the present invention, but do not exemplify the full scope of the invention.

Example 1

In this example, the effects of pressure were studied. Two supercritical fluid chromatography (SFC) systems were used: (1) a custom-made system by CF Technologies, Inc. (CFT system); and (2) an automated Waters Corporation Investigator system (Waters System). The CFT system was equipped with a Waters Acquity UPC UV/visible detector (Hyde Park, Mass., USA), and the Waters system was equipped with a Waters 2998 UV/visible detector (Milford, Mass., USA). UV spectra were used to identify the composition of each peak in the chromatograms. Initially, solutions comprising CBD were injected into the CFT system with pure $sCO_2$ solvent and a silica column at pressures ranging from 2000 to 5900 psi to examine effects of pressure on retention time. Through these experiments, it was confirmed that CBD eluted without co-solvents within the tested range of pressures. Subsequently, mixtures comprising three cannabinoids were injected into the systems at pressures ranging up to 10,000 psi.

Figure 3:
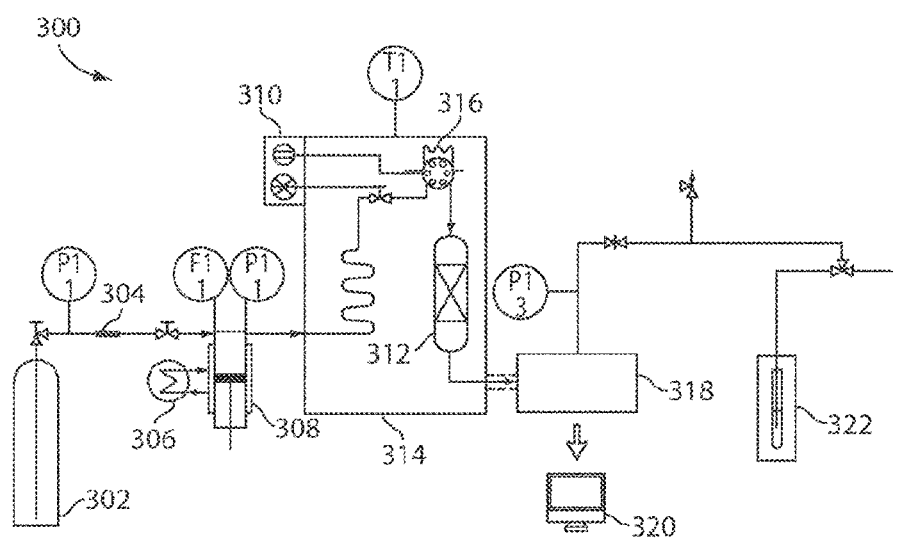
FIG. 3 shows, according to some embodiments, a schematic diagram of a chromatography system comprising a $CO_2$ tank, a chromatography column, a UV detector, and a sample collection device.

FIG. 3 shows a schematic diagram of CFT system 300. System 300 was designed for high-pressure operation, with a tubing pressure rating of 15,000 psi. As shown in FIG. 3, CFT system 300 comprised $CO_2$ tank 302, filter 304, chiller 306, syringe pump 308, valve control 310, column 312, convection oven 314, injection valve 316, UV detector 318, computer 320, and sample collection device 322.

Syringe pump (ISCO 260D, Teledyne, Nebr., USA) 308 was used to provide continuous flow of $CO_2$ through a tubing coil heat exchanger housed inside oven 314 operated at 40° C., where $CO_2$ achieved the supercritical state, followed by 6-port injection valve 316, packed column 312, and UV detector 318. A needle valve was placed after detector 318 to adjust the solvent flow rate. For operation at high pressures (e.g., above 6,000 psi), a second needle valve was added before the UV detector, and the Teledyne ISCO pump was replaced by a high-pressure pump. The high-pressure pump (unlike the Teledyne ISCO syringe pump) did not have a flow rate meter, and the flow rate was therefore estimated based on the known retention times. 6-port injection valve 316 was installed with a 5-μL injection loop. Injection valve 316 operated in two positions: (A) sample flowed through the external injection loop, while the solvent flowed directly into the column, and (B) the sample contained in the loop and valve flow passage was injected into the column.

Figure 4:
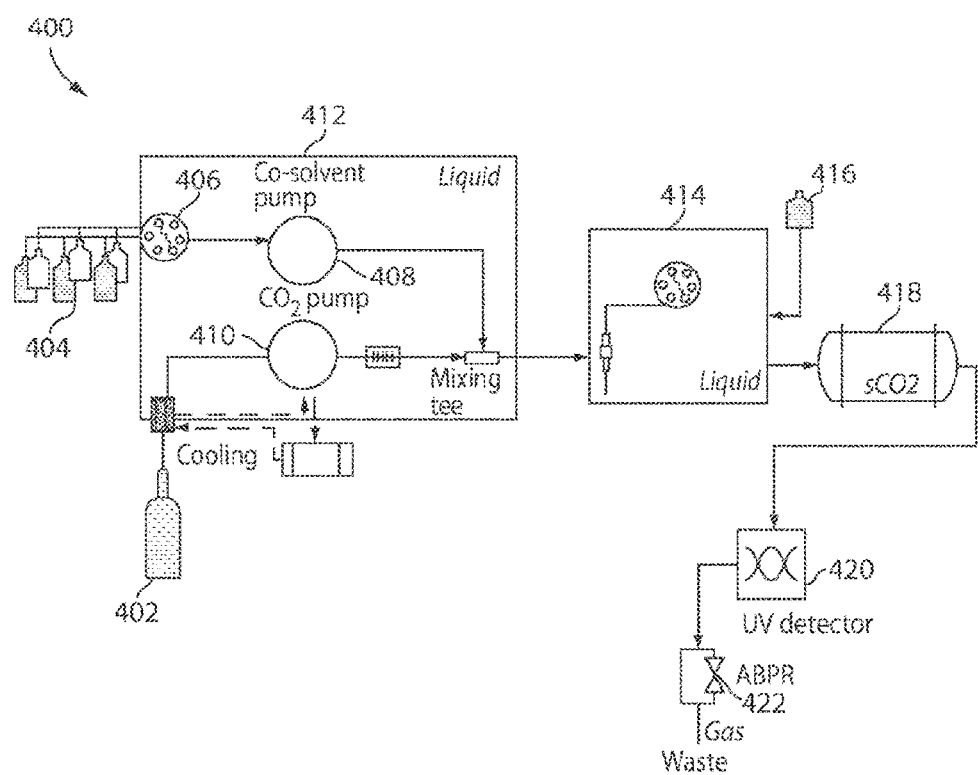
FIG. 4 shows a schematic diagram of a chromatography system comprising a $CO_2$ tank, a fluid delivery module, a column oven comprising a plurality of columns, and an auto back-pressure regulator, according to some embodiments.

FIG. 4 shows a schematic diagram of Waters system 400. Waters system 400 was designed for lower pressure experiments (e.g., 5,000 psi), and it was capable of operating both with and without co-solvents. As shown in FIG. 4, system 400 comprised $CO_2$ tank 402, co-solvent bottles 404, co-solvent selector 406, co-solvent pump 408, $CO_2$ pump 410, fluid delivery module (FDM) 412, auto-sampler 414, wash solvent 416, column oven 418, UV detector 420, and automatic back-pressure regulator (ABPR) 422.

Using FDM 412, subcooled solvent was continuously flowed through auto-sampler 414, column oven 418 operated at 40° C., UV detector 420, and ABPR 422. FDM 412 prepared the solvent to the desired composition of $CO_2$ and co-solvent. A 10 μL sample loop installed in auto-sampler 414 was cleaned with methanol after each injection. Up to ten columns were installed in oven 418 for rapid sequential assessment of adsorbent packing materials. ABPR 422 automatically adjusted needle valve positions to regulate the backpressure of the system during experimentation.

Retention times obtained from chromatograms were used to calculate equilibrium constant at several pressures, and then correlated to density and solubility. Data on the pressure, solubility, and density of $CO_2$ were fitted to identify the relationships between each parameter.

The compounds CBD and CP-47497 were purchased from Cayman Chemical (MI, USA) as 10 mg/ml stock solutions in methanol. Three cannabinoids in a mixture: CBD, CBN, and $\Delta^9$-THC were prepared by Waters Corporation (MA, USA), each as a 0.1 mg/mL stock solution in methanol. An additional mixture of the three cannabinoids was purchased from Sigma-Aldrich Corporation (MA, USA), each analyte as a 1.0 mg/mL stock solution in methanol. The mixture was diluted to a 0.1 mg/mL stock solution for use in the CFT system, while the original concentration of 1.0 mg/mL was used in the Waters system. SFC-grade liquid $CO_2$ was used as received from Airgas (MA, USA). Methanol of 99.8% purity from Sigma-Aldrich Corporation was used as a co-solvent in certain comparative experiments and in the sample injection module as cleaning fluid. A Viridis™ Silica column (5 μm, 4.6 mm×150 mm) donated by Waters Corporation was used in the CFT system. Viridis™ HSS C18 SB (1.8 μm, 3.0 mm×100 mm) and Acquity UPC BEH 2-EP (1.7 μm, 3.0 mm×50 mm) columns were used with the Waters SFC system.

Figure 5:
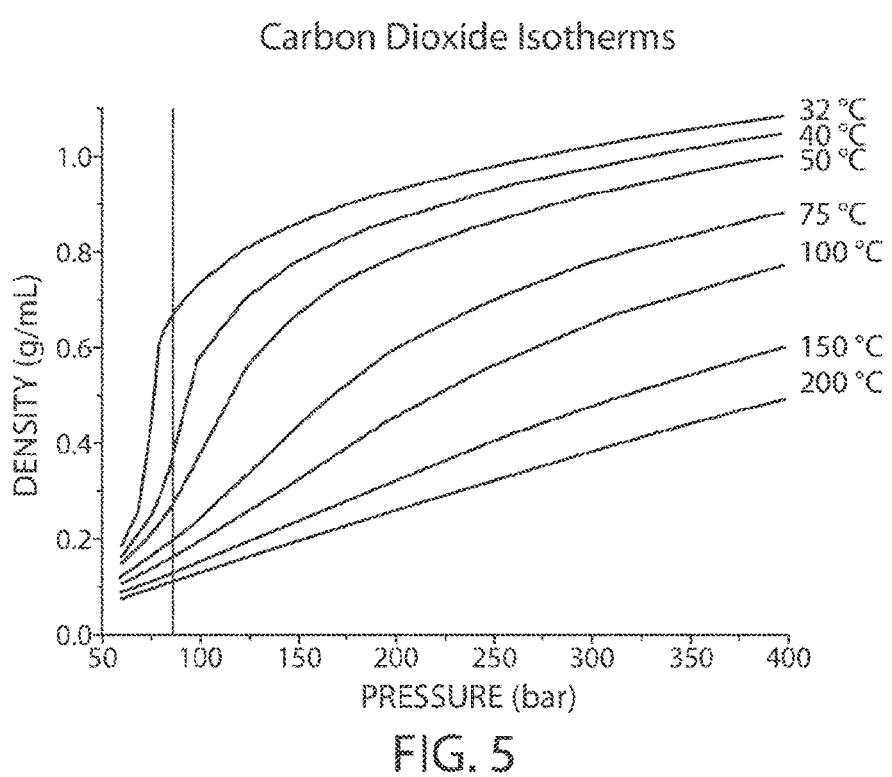
FIG. 5 shows, according to some embodiments, a plot of density as a function of pressure for carbon dioxide for different isotherms.

FIG. 5, which displays density versus pressure for different isotherms of carbon dioxide, therefore defining the limits of operation in the supercritical fluid region, demonstrates the benefits of varying pressure. The supercritical temperature of $CO_2$ is 304.25 K, and the pressure modulation study was operated at 313.15 K. The pressures investigated ranged from 1,100 psi to 10,000 psi. The density of $CO_2$ varied from 238 kg/m³ to 1042 kg/m³ over this pressure range. The effects of pressure on density were most pronounced when the reduced density of $CO_2$ was near unity (e.g., at its critical density), as it was relatively easy to compress. However, as the reduced density increased, the $CO_2$ became more resistant to further compression, and there was a smaller increase in density with increased pressure.

Figure 6A:
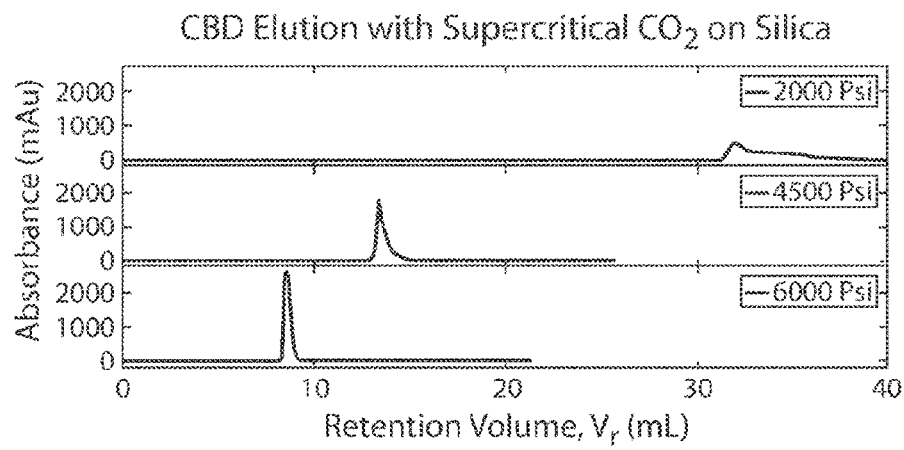
FIG. 6A shows chromatograms for a CBD solution run on a silica column with supercritical $CO_2$ at 40° C. at pressures of 2000 psi, 4500 psi, and 6000 psi, according to some embodiments.

The effects of pressure were assessed with the CFT system using CBD injections at different pressures and with a Viridis™ Silica column. A 5 μL sample of CBD was injected into the CFT system at multiple pressures to determine a pressure range for elution and to observe how the separation changes with pressure. The range of 2000 to 6000 psi was investigated. Chromatograms for the three CBD injections are shown in FIG. 6A. The retention volume decreased from 31 mL to 8.5 mL as the pressure increased from 2000 psi to 6000 psi. The retention volume at the intermediate pressure of 4500 psi was 13 mL. Though the CBD was dissolved in methanol, a methanol peak was not observed as its absorbance is much lower than that of CBD.

Figure 6B:
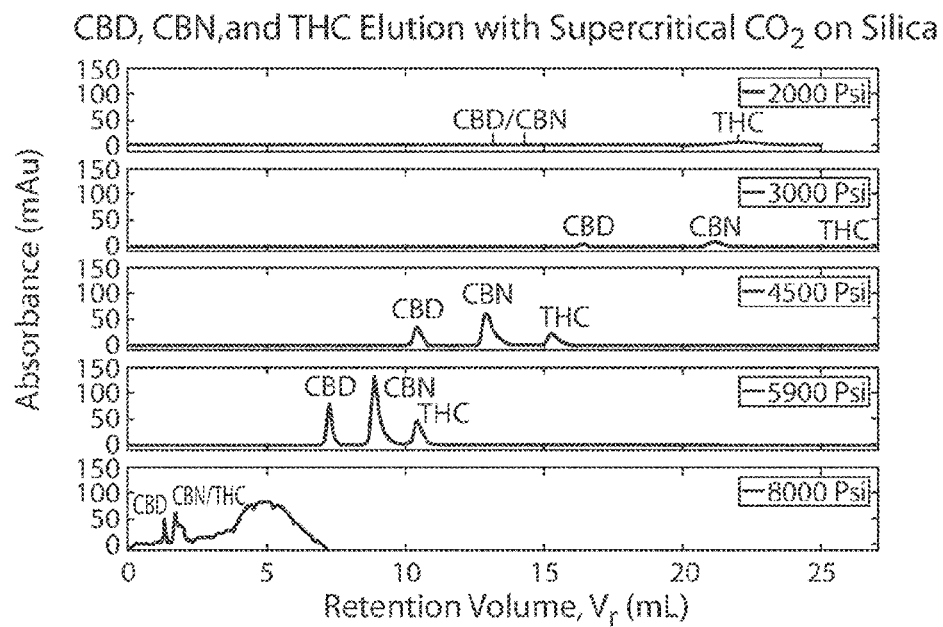
FIG. 6B shows chromatograms for a mixture comprising CBD, CBN, and THC run on a silica column with supercritical $CO_2$ at 40° C. at pressures ranging from 2000 psi to 8000 psi, according to some embodiments.

Once it was confirmed that CBD could be eluted using pure $CO_2$ at a pressure as low as 2000 psi using the CFT system, a mixture of CBD, CBN, and THC was injected to study effects of pressure on the separation of cannabinoid mixtures with the same silica column. All the CFT system injections of the three-cannabinoid mixture were performed using 0.1 mg/mL solution in methanol. A 5 μL mixture of CBD, CBN, and THC was injected using the same column in the CFT system. The pressures tested ranged from 2000 psi to 8000 psi. Chromatograms for five injections at different pressures are shown in FIG. 6B. The peaks for the chromatogram at 2000 psi are not visible on the scale presented, although elution for the three solutes was observed. Conditions for both CBD and the cannabinoid mixture injections are shown in Table 1.

TABLE 1

CF Technologies, Inc. SFC system operating conditions.

| a. Silica (CBD Solution) | | b. Silica (Mixture of 3) | |
|---|---|---|---|
| Flow Rate | 2-3 mL/min | Flow Rate | 2-3 mL/min |
| Column Temperature | 40° C. | Column Temperature | 40° C. |
| Sample Size | 5 μL | Sample Size | 5 μL |
| Solvent Base | $CO_2$ | Solvent Base | $CO_2$ |
| Co-solvent | — | Co-solvent | — |
| Co-solvent, % | — | Co-solvent, % | — |
| Pressure, psi | 2000-5900 | Pressure | 3000-10000 bar |
| PDA Range | 200-400 nm | PDA Range | 200-400 nm |

The retention volumes plotted for pressures above 6000 psi are rough estimates, and the chromatograms obtained for pressures above 6000 psi are therefore approximate. The pump used at pressures above 6000 psi did not have a flow rate indication, so the volumetric flow rate at 8000 psi was estimated by dividing the dead volume of the system by the time at which methanol eluted at 8000 psi. The fact that the flow rate may have been changing throughout the experiment, especially as pressure increased, may have contributed to the uncertainty surrounding the estimation.

The fractionation of the three-solute mixture was successful between 3000 and 5900 psi. At 2000 psi, THC separated from the mixture, while CBD and CBN remained mixed. At 8000 psi, CBD separated from the mixture while CBN and THC remained mixed.

The retention volume for each individual cannabinoid in a mixture changed with pressure, as seen in the prior experiments using only CBD. However, the relationship was not monotonic. From 2000 psi to 3000 psi, the retention volume of each solute increased. From 3000 psi to 8000 psi, the retention volume of each solute decreased as the pressure increased. Furthermore, the distance between peaks changed with pressure. Between 3000 psi and 5900 psi, the distance between each peak decreased as pressure increased. A comparison of the distance between peaks was not made using the chromatograms at 2000 psi and 8000 psi, since peaks merged.

Figure 7:
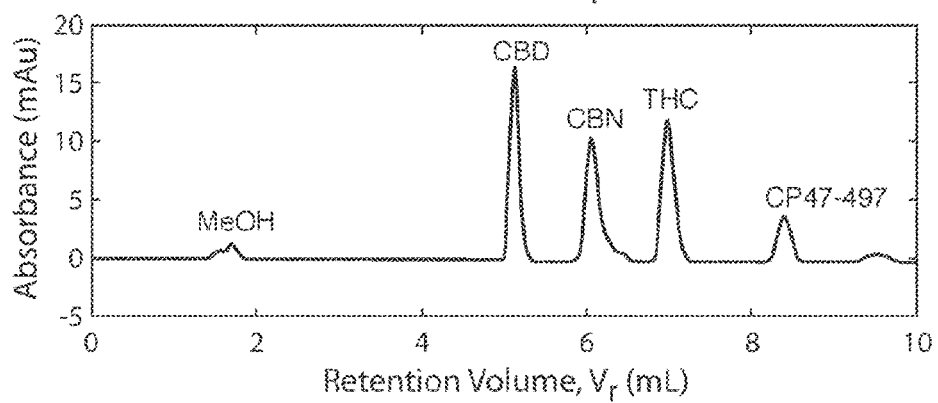
FIG. 7 shows, according to some embodiments, a chromatogram for a mixture comprising CBD, CBN, THC, and CP47-497 run on a silica column with supercritical $CO_2$ at 40° C. and 7500 psi.
Figure 8:
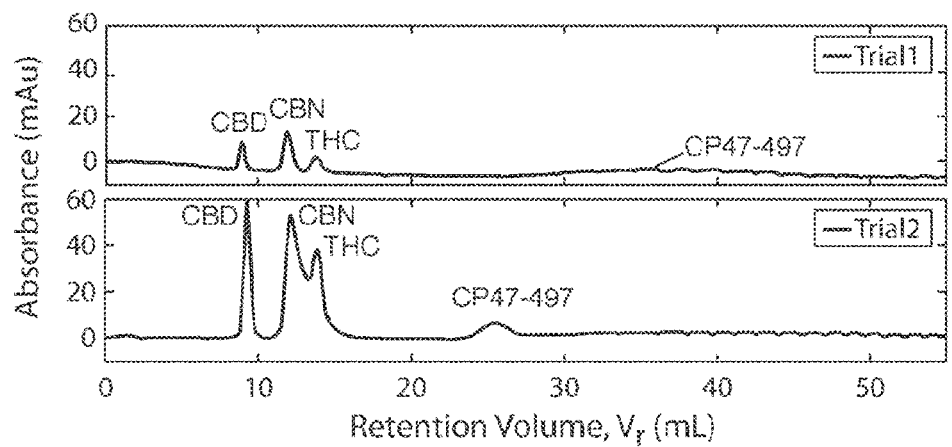
FIG. 8 shows chromatograms for a mixture comprising CBD, CBN, THC, and CP47-497 run on a silica column with supercritical $CO_2$ at 40° C., where pressure was stepped from 6000 psi to 10000 psi in 500 psi increments.

A fourth solute, CP-47497, was added to the previously examined three-solute mixture of CBD, CBN, and THC. Two types of experiments were performed. The first experiment was carried out at 7500 psi, the chromatogram for which is presented in FIG. 7. The second experiment was performed using a pressure gradient, in which the pressure was initially set to 6000 psi, and once the three natural cannabinoids were eluted, the pressure was raised to 10,000 psi in 500 psi increments every 10 seconds throughout the experiment. Two trials were conducted for the pressure gradient experiment, although the pressure profile was different for each trial because the pressure steps were performed manually (FIG. 8). Pressures above 6000 psi were used for these experiments because CP-47497 previously failed to elute at lower pressures. As seen in FIG. 8, all four solutes eluted separately. Although CP-47497 was successfully fractionated in the pressure step experiment, FIG. 8 shows that the CBN and THC peaks merged in one of the trials.

Figure 9A:
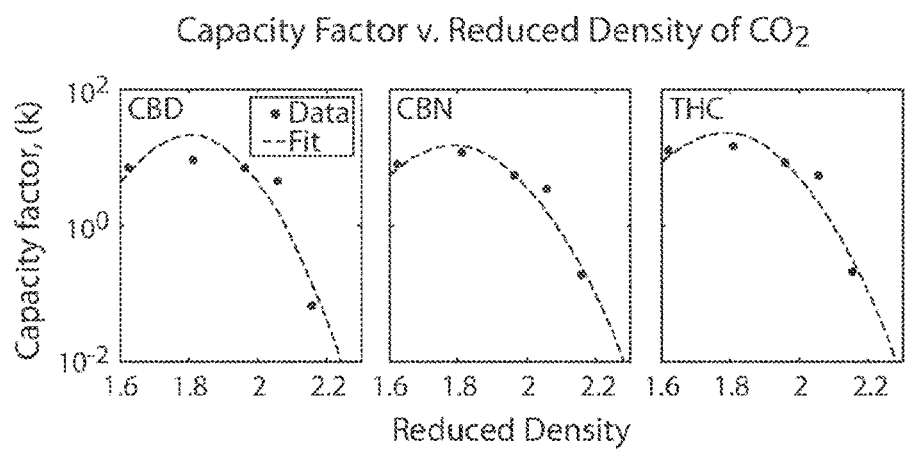
FIG. 9A shows, according to some embodiments, exemplary plots of capacity factor (using data from experiments run on silica with supercritical $CO_2$ at 40° C.) as a function of reduced density of $CO_2$ for CBD (left), CBN (middle), and THC (right)
Figure 9B:
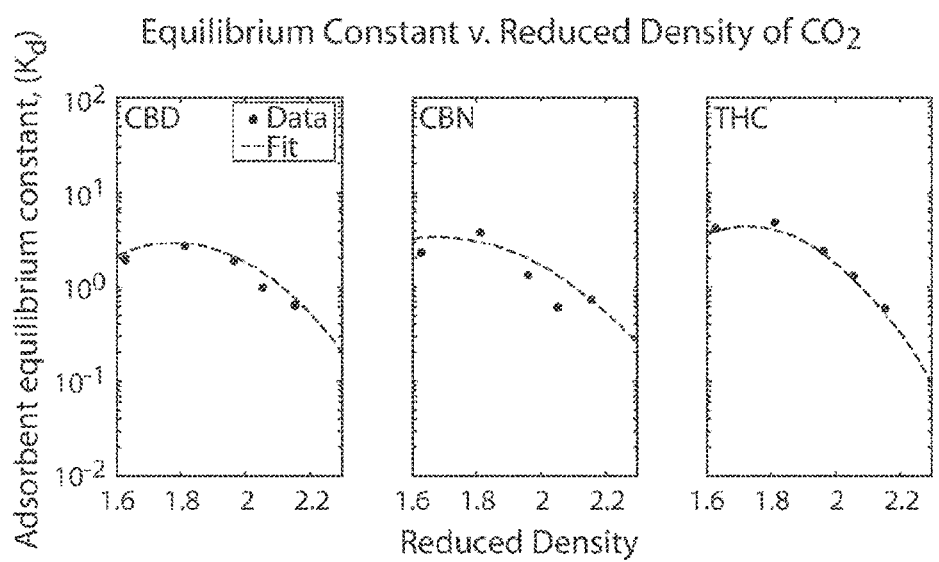
FIG. 9B shows, according to some embodiments, exemplary plots of equilibrium constant (using data from experiments run on silica with supercritical $CO_2$ at 40° C.) as a function of reduced density of $CO_2$ for CBD (left), CBN (middle), and THC (right)

Using data from experiments on the CFT equipment, the capacity factor and equilibrium constant were plotted against reduced density of $CO_2$. The data was fitted and is shown in Table 2. The capacity factor for each solute was calculated and density data was obtained from the literature. FIGS. 9A and 9B indicate that there exists a maximum for the capacity factor and equilibrium constant for each solute, rather than a monotonic relationship. Increasing the density of $CO_2$ increased the capacity factor and equilibrium constant at densities lower than the density that maximized the capacity factor (left side of the curve). Increasing the critical density beyond capacity factor maximizing density reduced the capacity factor and equilibrium constant (right side of the curve).

TABLE 2

Capacity factor and equilibrium constant fitted as functions of reduced density based on the CFT system experimental data for CBD, CBN, and THC.

| | CBD | CBN | THC |
|---|---|---|---|
| ln(k') | $-40.6\rho_r^2 + 146\rho_r - 129$ | $-30.6\rho_r^2 + 109\rho_r - 94.7$ | $-31.4\rho_r^2 + 112\rho_r - 96.7$ |
| ln($K_d$) | $-10.1\rho_r^2 + 36\rho_r - 31$ | $-6.6\rho_r^2 + 22.1\rho_r - 17.3$ | $-11.7\rho_r^2 + 40.4\rho_r - 33.4$ |

Figure 10:
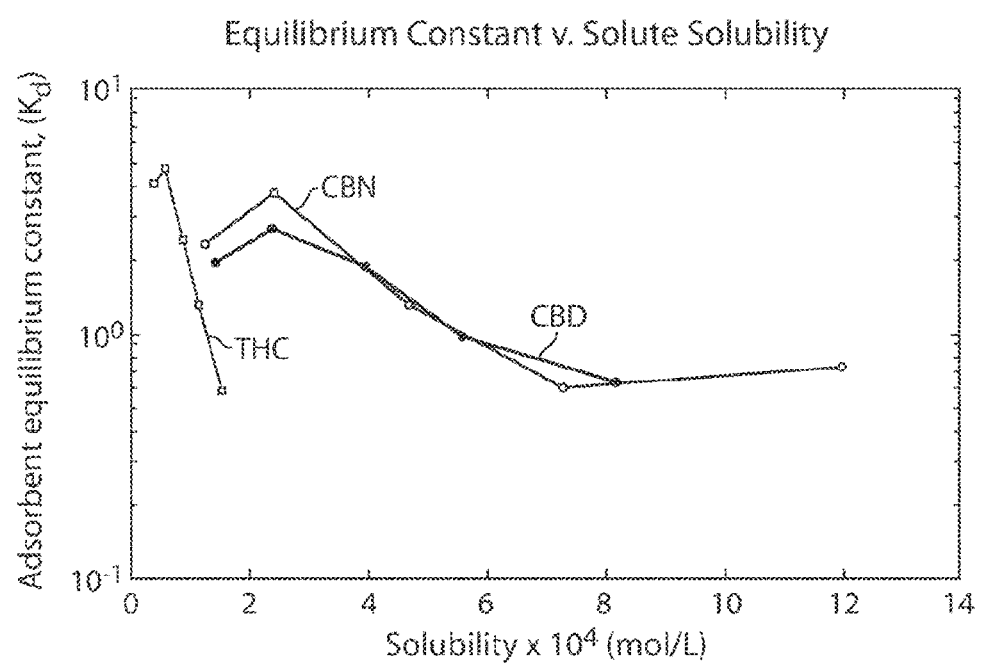
FIG. 10 shows an exemplary plot of equilibrium constant (using data from experiments run on silica with supercritical $CO_2$ at 40° C.) as a function of solubility for CBD, CBN, and THC, according to some embodiments.

The equilibrium constant for each solute was plotted against the solubility in $CO_2$ (FIG. 10). The solubility of CBD, CBN, and THC in $CO_2$ were obtained from the literature, and the correlations were fitted using the density-solubility correlation described and are shown in Table 3. The observed trend is similar to that seen in FIGS. 9A-B, where there exists a maximum for each solute, based on the obtained experimental data.

TABLE 3

Solubility correlation fitted as a function of pressure and density based on literature values.

| | CBD | CBN | THC |
|---|---|---|---|
| S(P) | $(0.5 \pm 0.05)P^{1.3\pm0.3}$ | $(0.02 \pm 0.01)P^{1.6\pm0.3}$ | $(0.03 \pm 0.07)P^{1.0\pm1.0}$ |
| S($\rho$) | $(4.6 \pm 2.0)10^{-5}\rho^{3.6\pm0.8}$ | $(3 \pm 3.0) \times 10^{-8}\rho^{6.0\pm1.0}$ | $(4 \pm 36) \times 10^{-5}\rho^{3.2\pm3.0}$ |

Example 2

In this example, the effects of temperature were examined with $C_{18}$ packing adsorbent material to observe the effects on the equilibrium constant for temperatures within and outside of the supercritical region at 1450 psi.

Two temperatures were studied: 0.0° C. and 40.0° C. The former temperature was in the liquid $CO_2$ region, where the density was 974 kg/m³, and the latter temperature lay within the supercritical $CO_2$ region, where the density was 630 kg/m³. Studying these two temperatures allowed a comparison of the performance of supercritical and liquid $CO_2$ chromatography as well as the effects of temperature with $C_{18}$, which is a hydrophobic packing material containing long hydrocarbon chains.

The Waters system described in Example 1 was used to observe the effects of temperature using $C_{18}$ at a constant pressure of 1450 psi. Temperatures of 0° C. and 40° C. were examined with pure $CO_2$ solvent and the 1.0 mg/mL three-cannabinoid mixture solution in methanol described in Example 1. Table 4 provides a full list of conditions.

TABLE 4

Waters Corporation Investigator SFC system operating conditions for temperature study. $C_{18}$ (1.0 mg/mL Mixture of 3)

| | |
|---|---|
| Flow Rate | 1.0 mL/min |
| Column Temperature | 0° C. and 40° C. |
| Sample Size | 1 µL |
| Solvent Base | $CO_2$ |
| Co-solvent | — |
| Co-solvent, % | — |
| Backpressure, psi | 1450 |
| Pressure Drop, psi | 870 |
| PDA Range | 220-300 nm |

Figure 11:
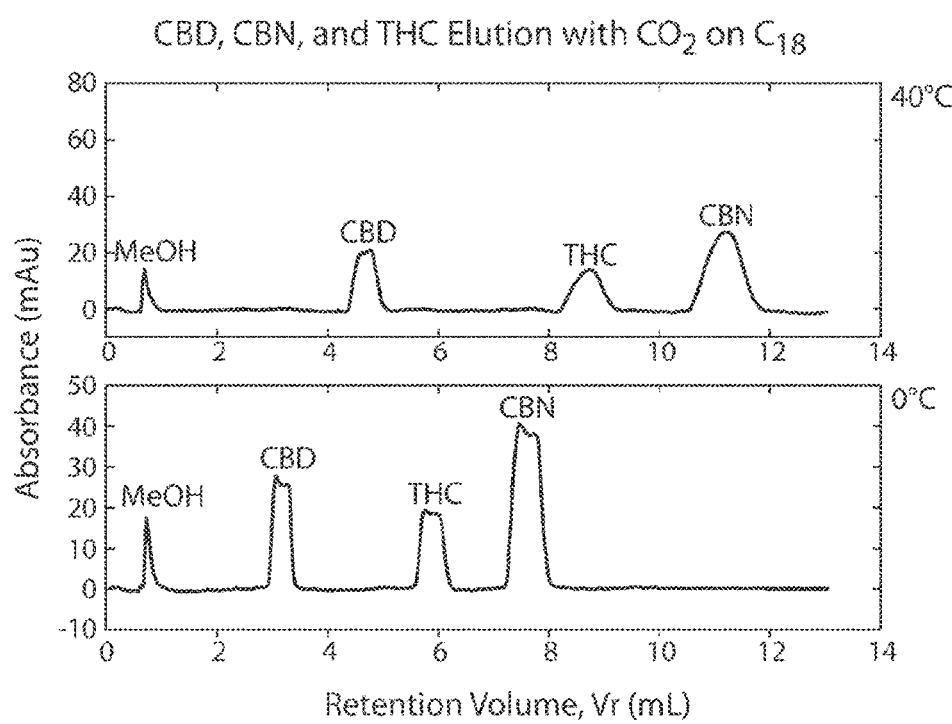
FIG. 11 shows, according to some embodiments, exemplary chromatograms of a mixture comprising CBD, CBN, and THC run on a $C_{18}$ column with $CO_2$ at temperatures of 0° C. and 40° C.

A $C_{18}$ (FIG. 11) column was used to separate the three-cannabinoid mixture (1.0 mg/mL) at 0° C. and 40° C. to examine the difference between the performance of supercritical and liquid $CO_2$. It was found that retention volume decreased with lower temperature and the retention time of the cannabinoid peaks decreased by about 30% as the temperature was lowered. The shape of the peaks also became slightly more distorted at lower temperature.

Example 3

The same mixture of CBD, CBN, and THC (0.1 mg/mL solution in methanol) described in Example 1 was investigated with Viridis™ HSS C18 SB and Acquity UPC BEH 2-EP columns at co-solvent concentrations varying from 0 to 10% in the Waters system described in Example 1. These co-solvent concentrations were examined at pressures of 1450 to 4000 psi to observe how the two solubility-enhancing effects of pressure and co-solvent behaved when combined. The Waters system was operated under the conditions tabulated in Table 5.

TABLE 5

Waters Corporation Investigator SFC system operating conditions for co-solvent study. $C_{18}$/BEH 2-EP (CBD and Mixture of 3)

| | |
|---|---|
| Flow Rate | 1.0-3.0 mL/min |
| Column Temperature | 40° C. |
| Sample Size | 1 µL |
| Solvent Base | $CO_2$ |
| Co-solvent | MeOH |
| Co-solvent, % | 0-10 |
| Backpressure, psi | 1450-4000 |
| Pressure Drop, psi | 800-870 |
| PDA Range | 220-300 nm |

Figure 12A:
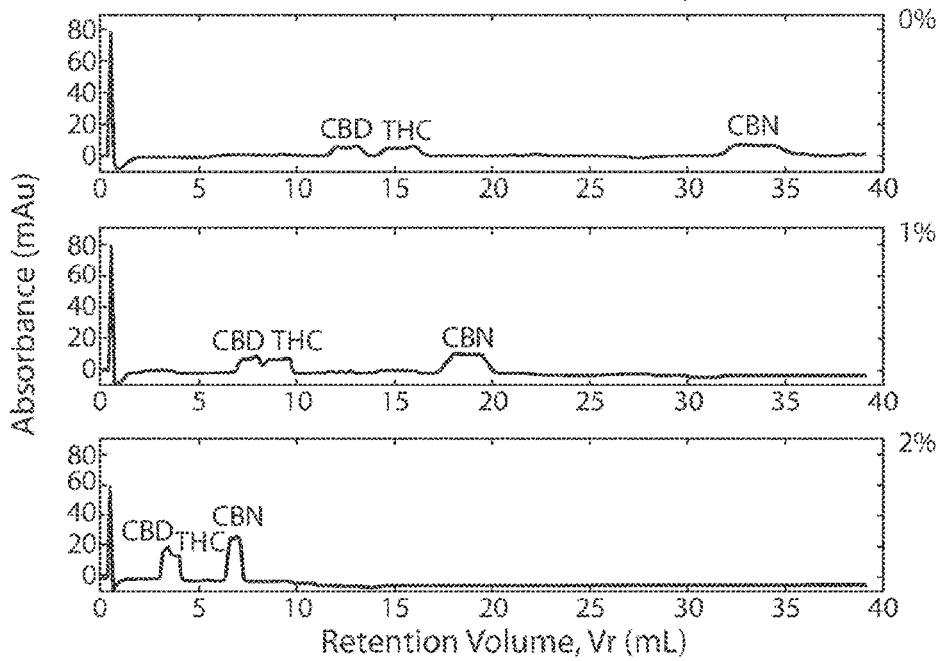
FIG. 12A shows exemplary chromatograms for a mixture comprising CBD, CBN, and THC run on a BEH 2-EP (i.e., silica coated with ethyl pyridine) column with $CO_2$ and 0-2% methanol (MeOH) co-solvent at 40° C. and 1450 psi, according to some embodiments.
Figure 12B:
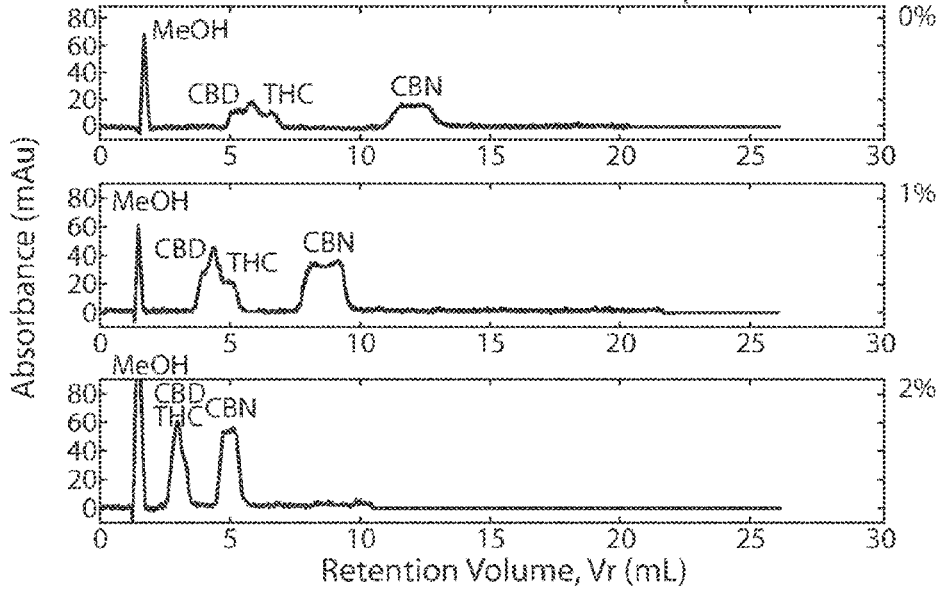
FIG. 12B shows exemplary chromatograms for a mixture comprising CBD, CBN, and THC run on a BEH 2-EP column with $CO_2$ and 0-2% methanol co-solvent at 40° C. and 4000 psi, according to some embodiments.

BEH 2-EP and $C_{18}$ columns were investigated using co-solvent concentrations of 0 to 2%. The BEH 2-EP column was examined with $CO_2$ and 0 to 2% methanol co-solvent at 1450 psi (FIG. 12A) and 4000 psi (FIG. 12B) with a 1.0 mg/mL three-cannabinoid mixture using the Waters system. It was observed with BEH 2-EP that faster elution was seen at higher pressure and higher co-solvent concentration. The THC peak remained close to the CBD when eluted using pure $CO_2$.

Figure 13:
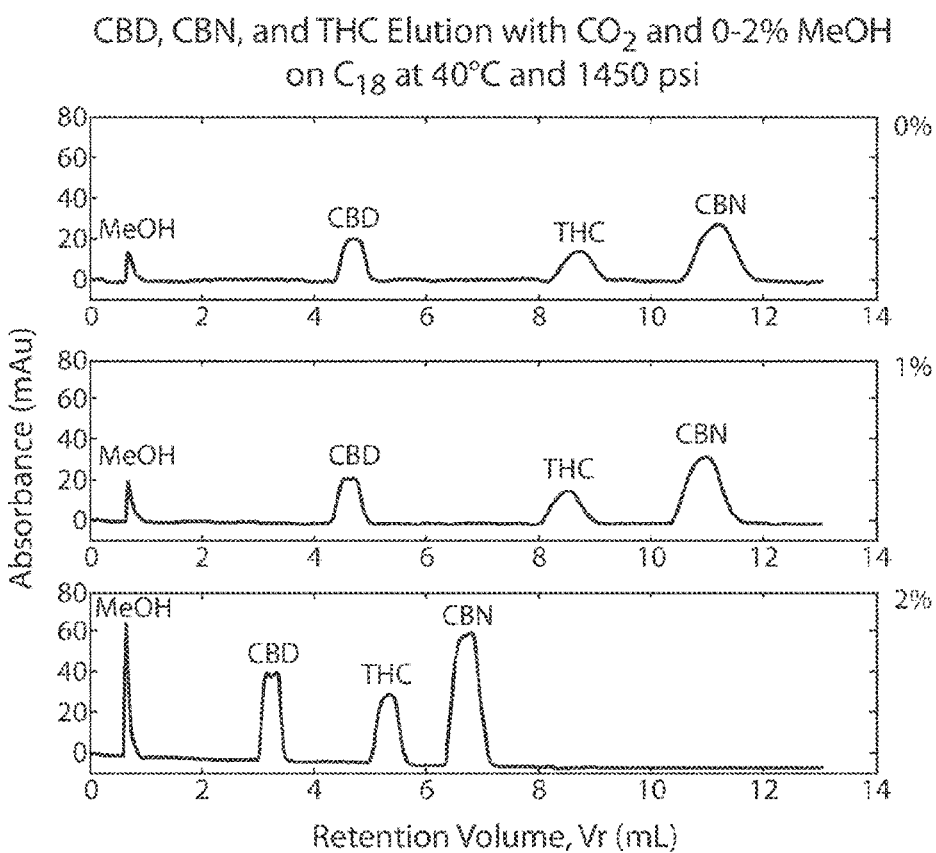
FIG. 13 shows, according to some embodiments, exemplary chromatograms of a mixture of CBD, CBN, and THC run on a $C_{18}$ column with $CO_2$ and 0-2% methanol co-solvent at 40° C. and 1450 psi.

$C_{18}$ was investigated at 1450 psi with a 1.0 mg/mL three-cannabinoid mixture using $CO_2$ and 0 to 2% of methanol co-solvent (FIG. 13). Among the examined adsorbents, $C_{18}$ had the lowest retention volume when used with pure $CO_2$. It was the only column that provided clear separation of all three cannabinoids in the Waters system. THC was eluted closer to CBN, unlike with BEH 2-EP. Lastly, there was marginal difference between the separation with pure $CO_2$ and 1% methanol co-solvent. In both cases, the retention volumes were almost identical, with only slight differences in the width of the peaks. A more significant difference in the peak width was observed between 0-1% and 2%. At 2% methanol co-solvent, the peaks were narrower than those for lower co-solvent percentage runs. However, overall the shape of the peaks eluted using the $C_{18}$ column was significantly better than that of the BEH 2-EP column.

Figure 14:
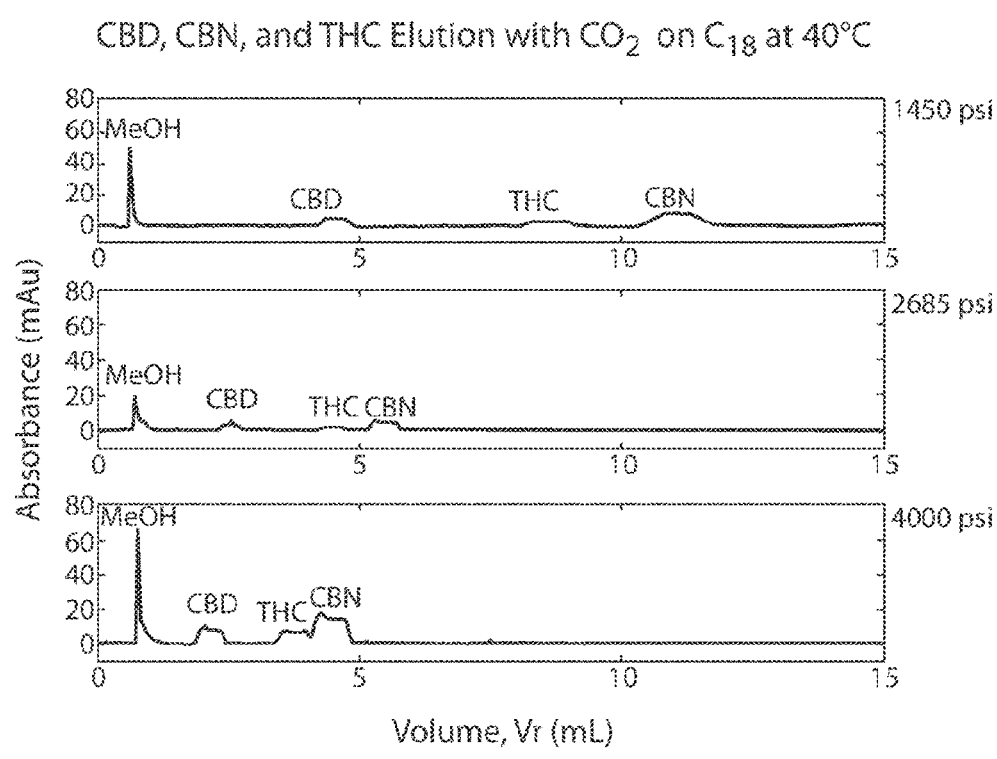
FIG. 14 shows exemplary chromatograms of a mixture of CBD, CBN, and THC run on a $C_{18}$ column with $CO_2$ at 40° C. and 1450 psi, 2865 psi, and 4000 psi, according to some embodiments.

$C_{18}$ was additionally investigated using the 0.1 mg/mL three-cannabinoid mixture with pure $CO_2$ at 1450, 2685, and 4000 psi using the Waters system (FIG. 14). As the pressure was increased, the retention volume and the distance between the peaks decreased. At 4000 psi, the THC and CBN peaks began to overlap. There was a larger difference in retention volume between 1450 and 2685 psi when compared to that between 2685 and 4000 psi.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Having thus described several aspects of at least one embodiment, it is to be appreciated that various alterations, modifications, and improvements will readily occur to those skilled in the art. Such alterations, modifications, and improvements are intended to be within the spirit and scope of the present disclosure. Accordingly, the foregoing description and drawings are by way of example only.

Various features and aspects of the present disclosure may be used alone, in any combination of two or more, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the concepts disclosed herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall be interpreted as having the same meaning as "and/or" as defined above and shall not be interpreted as indicating exclusive alternatives (i.e. "one or the other but not both") unless preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A chromatography method for purifying a cannabis-derived compound from a mixture, comprising:
    transporting the mixture, which comprises a first component and a second component, through a chromatography column containing a stationary phase comprising a packing material, wherein the first component comprises a first cannabis-derived compound, wherein the mixture is transported within a mobile phase that comprises carbon dioxide and is substantially free of a co-solvent that is in liquid phase at standard room temperature and pressure through the column and in contact with the stationary phase, and wherein the first component and the second component of the mixture are each transported within the mobile phase substantially continuously from a first end of the column to a second end of the column;
    collecting from the second end of the column a first fraction of the mobile phase comprising the first component over a first time interval, wherein the first fraction is substantially free of the second component; and
    collecting from the second end of the column a second fraction of the mobile phase comprising the second component over a second time interval different from the first time interval, wherein the second fraction is substantially free of the first component.

2. The chromatography method according to claim 1, wherein the mobile phase is substantially free of any co-solvent.

3. The chromatography method according to claim 1, wherein the carbon dioxide comprises supercritical carbon dioxide.

4. The chromatography method according to claim 3, wherein the transporting step is performed at a temperature in a range between about 31° C. and 70° C. and a pressure in a range between about 1,085.7 psi and about 30,000 psi.

5. The chromatography method according to claim 1, wherein the carbon dioxide comprises liquid carbon dioxide.

6. The chromatography method according to claim 5, wherein the transporting step is performed at a temperature in a range between about 0° C. and about 30° C. and/or a pressure in a range between about 500 psi and about 10,000 psi.

7. The chromatography method according to claim 1, wherein the concentration of carbon dioxide in the mobile phase is at least about 80 vol %.

8. The chromatography method according to claim 1, wherein the concentration of carbon dioxide in the mobile phase is about 100 vol %.

9. The chromatography method according to claim 1, wherein the mobile phase comprises a co-solvent or diluent that is in gaseous phase at standard room temperature and pressure.

10. The chromatography method according to claim 9, wherein the concentration in the mobile phase of the co-solvent that is in gaseous phase at standard room temperature and pressure is about 20 vol % or less.

11. The chromatography method according to claim 9, wherein the co-solvent that is in gaseous phase at standard room temperature and pressure is nitrous oxide, dimethyl ether, ethane, propane, butane, sulfur hexafluoride, and/or a halocarbon.

12. The chromatography method according to claim 1, wherein the first cannabis-derived compound comprises cannabidiol (CBD), cannabinol (CBN), and/or tetrahydrocannabinol (THC).

13. The chromatography method according to claim 1, wherein the second component comprises a second cannabis-derived compound.

14. The chromatography method according to claim 1, wherein the mixture further comprises a third component comprising a third cannabis-derived compound.

15. The chromatography method according to claim 14, further comprising collecting a third fraction of the mobile phase comprising the third component over a third time interval different from the first time interval and the second time interval, and wherein the third fraction is substantially free of the first component and the second component.

16. The chromatography method according to claim 1, wherein the packing material comprises silica, BEH 2-EP, and/or $C_{18}$.

17. The chromatography method according to claim 1, wherein the first component comprises at least about 50 wt % of components of the mixture transported within the mobile phase collected in the first fraction.

18. The chromatography method according to claim 1, wherein the second component comprises at least about 50 wt % of components of the mixture transported within the mobile phase collected in the second fraction.

19. A chromatography system for purifying a first cannabis-derived compound from a mixture, comprising:

a chromatography column containing a stationary phase comprising a packing material;

a mobile phase comprising carbon dioxide, wherein the mobile phase is substantially free of a co-solvent that is in liquid phase at standard room temperature and pressure; and the mixture, wherein the mixture comprises a first component and a second component, wherein the first component comprises the first cannabis-derived compound.

20. The chromatography system according to claim 19, wherein the mobile phase is substantially free of any co-solvent.

21. The chromatography method according to claim 1, wherein each fraction collected from the second end of the column is substantially free of any co-solvent.

22. The chromatography method according to claim 1, wherein the first component comprises at least about 95 wt % of components of the mixture transported within the mobile phase collected in the first fraction.

23. The chromatography system according to claim 19, wherein the first component comprises at least about 95 wt % of components of the mixture within the mobile phase at an exit of the chromatography column.

* * * * *